(12) United States Patent
Pauletti et al.

(10) Patent No.: US 7,744,916 B2
(45) Date of Patent: Jun. 29, 2010

(54) COATED VAGINAL DEVICE FOR DELIVERY OF ANTI-MIGRAINE AND ANTI-NAUSEA DRUGS

(75) Inventors: Giovanni M. Pauletti, Loveland, OH (US); Michelle Wilson, Hamilton, OH (US); Richard Soderstrom, Seattle, WA (US); Desai J. Kishorkumar, Westchester, OH (US); Wolfgang A. Ritschel, Cincinnati, OH (US)

(73) Assignee: UMD, Inc., Cincinnati, OH (US)

( * ) Notice: Subject to any disclaimer, the term of this patent is extended or adjusted under 35 U.S.C. 154(b) by 1389 days.

(21) Appl. No.: 11/126,863

(22) Filed: May 10, 2005

(65) Prior Publication Data
US 2005/0249774 A1 Nov. 10, 2005

Related U.S. Application Data

(63) Continuation-in-part of application No. 10/600,849, filed on Jun. 20, 2003, and a continuation-in-part of application No. 10/349,029, filed on Jan. 22, 2003, now Pat. No. 6,905,701, and a continuation-in-part of application No. 10/226,667, filed on Aug. 21, 2002, now Pat. No. 6,982,091, which is a continuation-in-part of application No. 09/626,025, filed on Jul. 27, 2000, now Pat. No. 6,572,874, which is a continuation-in-part of application No. 09/249,693, filed on Feb. 12, 1999, now Pat. No. 6,086,909, which is a continuation-in-part of application No. 09/079,897, filed on May 15, 1998, now Pat. No. 6,197,327.

(60) Provisional application No. 60/587,454, filed on Jul. 12, 2004, provisional application No. 60/049,325, filed on Jun. 11, 1997.

(51) Int. Cl.
*A61F 6/06* (2006.01)
*A61F 6/14* (2006.01)
*A61F 13/02* (2006.01)

(52) U.S. Cl. ............... 424/433; 424/430; 424/432
(58) Field of Classification Search .............. None
See application file for complete search history.

(56) References Cited

U.S. PATENT DOCUMENTS 6,197,327 B1 * 3/2001 Harrison et al. ............. 424/430

(Continued)

FOREIGN PATENT DOCUMENTS

EP 391852 A2 * 10/1990

(Continued)

OTHER PUBLICATIONS

Patrick Henry, et al., A Nationwide Survey of Migraine in France: Prevalence and Clinical Features in Adults, *Cephalalgia*, 12:229-237, (1992).

(Continued)

*Primary Examiner*—Carlos A Azpuru
(74) *Attorney, Agent, or Firm*—Peters Verny, LLP; Hana Verny

(57) ABSTRACT

A vaginal device for delivery of an anti-migraine or anti-nausea drug to the uterus and/or to the general circulation through vaginal mucosa. The device is at least partially coated with one or several layers of fluid impermeable material forming a cap, film, foam, foil or strip incorporated with mucoadhesive composition comprising the anti-migraine or anti-nausea drug.

13 Claims, 5 Drawing Sheets

U.S. PATENT DOCUMENTS

2002/0055495 A1* 5/2002 Jannetta ................ 514/171

OTHER PUBLICATIONS

Lori A. Rokicki, PhD., et al., An Examination of the Validity of the IHS Classification System for Migraine and Tension-Type Headache in the College Student Population, *Headache*, 39:720-727, (1999).

Walter F. Stewart, PhD., MPH, et al., Prevalence of Migraine Headache in the United States, Relation to Age, Income, Race, and Other Sociodemographic Factors, *JAMA*, 267/1:64-69, (Jan. 1, 1992).

G.D. Solomon, et al., Burden of Migraine, a Review of its Socioeconomic Impact,*Pharmacoeconomics*, 11/1:1-10, (1997).

H. Vergin, et al., Analysis of Formulation and Food Effect on the Absorption of Metoclopramide,*International Journal of Clinical Pharmacology and Therapeutics*, 40/4:169-174, (2002).

* cited by examiner

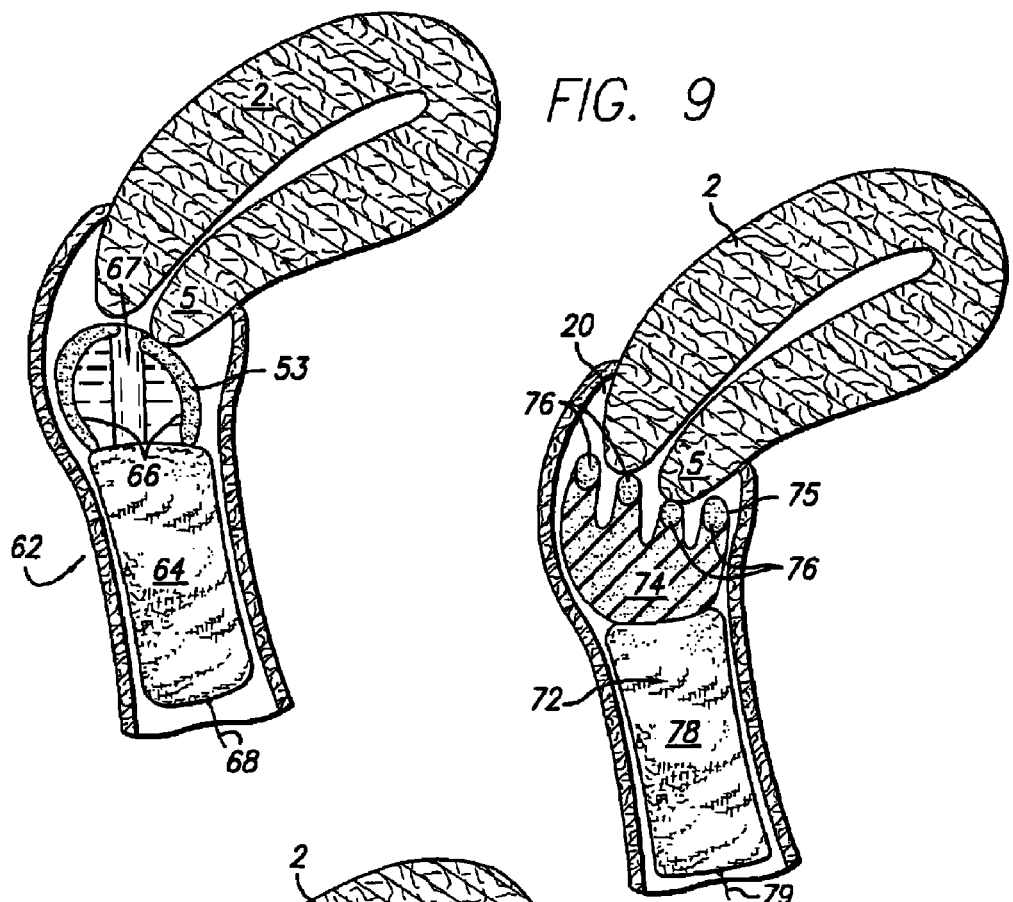
FIG. 9
FIG. 10
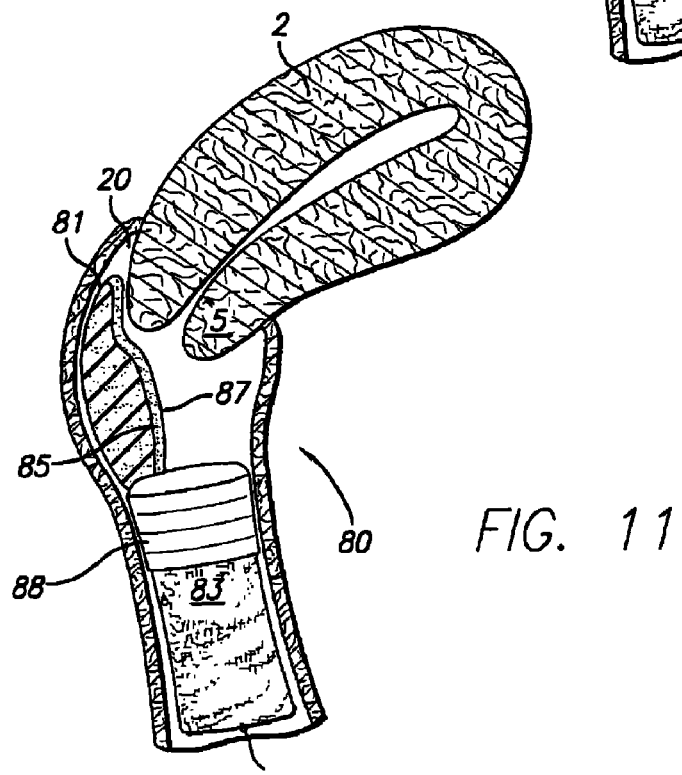
FIG. 11

COATED VAGINAL DEVICE FOR DELIVERY OF ANTI-MIGRAINE AND ANTI-NAUSEA DRUGS

This application claims priority of the Provisional application Ser. No. 60/587,454 and is a continuation-in-part of application Ser. No. 10/226,667 filed on Aug. 21, 2002 and a continuation-in-part of application Ser. No. 10/600,849, filed Jun. 20, 2003 and a continuation-in-part of application Ser. No. 10/349,029, filed Jan. 22, 2003, allowed, which is a continuation-in-part of application Ser. No. 09/626,025, filed Jul. 27, 2000, issued as U.S. Pat. No. 6,572,874 which is a continuation-in-part of application Ser. No. 09/249,963, filed Feb. 12, 1999, issued as U.S. Pat. No. 6,086,909, which is a continuation-in-part of the U.S. patent application Ser. No. 09/079,897, filed on May 15, 1998, issued as U.S. Pat. No. 6,197,327, which claims priority of the Provisional Application Ser. No. 60/049,325, filed Jun. 11, 1997, under 35 U.S.C.§111(b).

FIELD OF THE INVENTION

The present invention concerns a coated vaginal device for delivery of anti-migraine and/or anti-nausea drugs and a method for treatment of migraine and nausea. The vaginal device, such as a vaginal tampon, vaginal tampon-like foam or another vaginal device is completely or partially coated with one or several layers of a fluid impermeable coating material incorporated with a composition comprising an anti-migraine or anti-nausea drug, or a combination thereof, said composition formulated for delivery of said drug to the uterus and/or to the general circulation through vaginal mucosa. In particular, the invention concerns a targeted delivery of the anti-migraine or anti-nausea drug to the uterus or to the general circulation using the vaginal device such as a tampon, tampon-like foam or a tampon-like device which is coated or of which a portion is coated with one or several layers of a fluid impermeable material such as a film, foam, xerogel or foil forming a layer, cap, cup or a strip incorporated with said composition comprising said drug or a combination of drugs.

The method for treatment of migraine and/or nausea comprises a step of inserting a vaginal device coated with a fluid impermeable layer comprising a mucoadhesive composition into vagina wherein said composition is released from said impermeable coating layer into a vicinity of the uterus and the drug is transferred transmucosally directly to the uterus and/or to the general systemic circulation. The impermeable layer permits a quantitatively more controllable release of the drug as the drug is concentrated within the impermeable layer placed close to the uterus. The impermeable layer further insulates the drug from reabsorption to the non-medicated portion of the device and since it is typically placed on the proximal end of the device close to the uterus, assures the maximal contact of the drug with the vaginal mucosa close to the uterus. These features allow treatment of migraine or nausea with lower concentrations of the drug than those needed for oral administration and thus permit lower systemic concentrations and protect a subject from side effects caused by high concentrations of the anti-migraine or anti-nausea drugs required for oral use.

BACKGROUND OF THE INVENTION

Migraine is a chronic condition with recurrent episodic attacks. It is rather unpredictable illness with its characteristics varying among patients. This unpredictability and variability is also observed within migraine attacks observed in a single patient. Among the most distinguishing features of a migraine is a potential disability caused by the accompanying headache and nausea with or without vomiting as well as extreme sensitivity to sound and light (*Headache*, 39: 720-727 (1999)). Because of the variability and complexity of the condition, effective management of patients suffering from migraines is challenging.

Migraine headaches which are considered "primary headaches" are about three times more common in women than in men. Geographically, the occurrence of migraine headaches varies significantly and ranges from 1.5% in Southeast Asia to 14% in Western countries (*GRIM, Cephalalgia*, 12:229 (1992); *JAMA*, 267:64-69 (1992) and *Pharmacoeconomics*, 11: 1-10 (Suppl.1)(1997)).

Systemic administration of anti-migraine and anti-nausea drugs orally to patients has not been very successful, in part because migraine is often accompanied by nausea and the orally administered drugs are vomited before they can take effect. The only viable route of administration for treatment of nausea and/or migraine is the intravenous or another injectable administration. These typically require a visit at the doctor's office or hospital. The failure to successfully treat migraine or nausea is thus based on a delivery method rather than on the drug effectiveness.

The vaginal delivery route of drugs through the vaginal mucosa to the uterus and/or to the general circulation has been discovered by inventors and is disclosed, for example, in the U.S. Pat. Nos. 6,086,909, 6,197,327 and 6,572,874 and in a co-pending application Ser. No. 10/600,849 and 10/349,029, all hereby incorporated by reference.

As well as the vaginal delivery route described in the above cited patents and application works, there is still some need for improvement, particularly as it concerns an efficacious quantitative drug delivery.

The current invention thus concerns an improved transmucosal delivery of anti-migraine and anti-nausea drugs through vaginal mucosa directly to uterus or to the general circulation which is more efficacious due to a more quantifiable sequestration of the drug within the impermeable layer or layers covering a proximal portion of the vaginal device.

It is therefore a primary objective of this invention to provide a vaginal device, such as a tampon, tampon-like foam or another vaginal device which is coated, or of which a proximal portion is coated, with a fluid impermeable layer(s) of film, foil, foam or xerogel forming a strip or an attached or removable cap or cup wherein said impermeable layer further comprises a mucoadhesive composition comprising an anti-migraine or anti-nausea drug, or a combination of both, said composition being released and delivered from said layer(s) substantially quantitatively through the vaginal mucosa into the uterus and/or to the general circulation.

SUMMARY OF THE INVENTION

One aspect of the current invention is a vaginal device completely or partially coated with a layer or layers of the fluid impermeable material such as an impermeable film, foam, foil or xerogel forming a strip or an attached or removable cap or cup, said layer(s) being completely or partially incorporated with a mucoadhesive composition comprising a therapeutic and/or palliative amount of an anti-migraine or anti-nausea drug.

Another aspect of the current invention is a vaginal tampon, tampon-like foam or another vaginal device coated with a layer or layers of the fluid impermeable material such as an impermeable film, foam, foil or xerogel forming an attached or removable cap, cup or strip, said layer(s) incorporated with a composition comprising a therapeutic and/or palliative amount of the anti-migraine or anti-nausea drug for delivery to the uterus and/or to the general circulation through vaginal wall.

Still another aspect of the current invention is a method for targeted delivery of drugs to the uterus or to the general circulation using a vaginal device which is coated, or of which a proximal portion closest to uterus is coated, with a fluid impermeable layer or layers of material such as a impermeable film, foam, foil or xerogel forming an attached or removable cap, cup or strip, said layer(s) incorporated with a mucoadhesive composition comprising an anti-migraine or anti-nausea drug or a combination thereof.

Still another aspect of the current invention is a method for targeted delivery of drugs to the uterus or to the general circulation using a vaginal tampon, tampon-like foam or another vaginal device of which a proximal portion is covered with a fluid impermeable layer or layers of a coating material such as an impermeable film, foam, foil or xerogel forming an attached or removable cap, cup or strip, said layer(s) incorporated with a mucoadhesive composition comprising an anti-migraine or anti-nausea drug, a combination thereof, or a combination of either an anti-migraine or anti-nausea drug with another therapeutically effective agent or pharmaceutically acceptable excipient.

Still yet another aspect of the current invention is a mucoadhesive composition comprising an anti-migraine or anti-nausea drug, or a combination thereof, incorporated into an impermeable layer(s) covering a proximal portion of a vaginal device wherein said impermeable layer(s) of the fluid impermeable coating material is an impermeable film, foam, xerogel or foil forming an attached or removable cap, cup or strip wherein said composition is quantitatively released from said layer(s) thereby delivering an effective amount of an anti-migraine or anti-nausea drug into the uterus or directly to the general circulation thereby bypassing the gastrointestinal tract.

Still another aspect of the current invention is a mucoadhesive composition for incorporation into an impermeable layer of a coating of a vaginal device wherein said composition comprises an anti-migraine or anti-nausea drug selected from the group consisting of ergot alkaloid, ergot alkaloid derivative, antihistamine, barbiturate, non-steroidal anti-inflammatory agent, analgesic, serotonin antagonist, neurokinin-1 antagonist, cannabinoid, calcitonin gene-related peptide (CGRP) antagonist, steroid, sympathomimetic, tranquilizer and anti-epileptic agent, each alone or in combination with an anti-nausea drug selected from the group consisting of metoclopramide, prochlorperazine, domperidone, ondansetron, tropisetron, dolasetron, nabilone, dronabinol, levonantradol, CP55940, SR 144528, aprepitant, cyclizine, and promethazine, BIBN-4096BS, SB-(+)-273779, each alone and/or further in combination with another therapeutically effective agent or a pharmaceutically acceptable excipient.

Still another aspect of the current invention a mucoadhesive composition comprising an anti-migraine drug selected from the group consisting of ergotamine, dihydroergotamine, ergostine, butalbital, phenobarbital, acetaminophen, diclofenac sodium, ketoprofen, ketorolac, ibuprofen, piroxicam, naproxen, acetylsalicylic acid, flurbiprofen, tolfenamic acid, butorphanol, meperidine, methadone, sumatriptan, naratriptan, razatriptan, zolmitriptan, almotriptan, eletriptan, dexamethasone, hydrocortisone, isometheptene, chlorpromazine, diazepam, droperidol, valproic acid, gabapentin, topiramate, divalproex sodium, or an anti-nausea drug selected from the group consisting of metoclopramide, prochlorperazine, domperidone, ondansetron, tropisetron, dolasetron, nabilone, dronabinol, levonantradol, CP55940, SR 144528, aprepitant, cyclizine, and promethazine, BIBN-4096BS and SB-(+)-273779, each alone or in combination, or further in combination with another therapeutically effective agent.

Another aspect of the current invention is a method for treatment, management and control of migraine and headache pain, nausea, and vomiting associated with migraine or other conditions, such as, for example, infection, pregnancy, poisoning, surgery, radiotherapy or administration of chemotherapeutic drugs, said method comprising steps of contacting vaginal mucosa with a vaginal device coated or partially coated with one or several layers of an impermeable coating material incorporated with a mucoadhesive composition, said composition comprising an anti-migraine drug selected from the group consisting of ergot alkaloid, ergot alkaloid derivative, antihistamine, barbiturate, non-steroidal anti-inflammatory agent, analgesic, serotonin antagonist, neurokinin-1 antagonist, cannabinoid, calcitonin gene-related peptide (CGRP) antagonist, steroid, sympathomimetic, tranquilizer and anti-epileptic agent, each alone or in combination with an anti-nausea drug and/or further in combination with another therapeutically effective agent or a pharmaceutically acceptable excipient and maintaining said device in contact with vaginal mucosa for a period of time permitting a quantitative, controlled, rapid or slow, continuous or pulsed delivery of the agent to and through the vaginal mucosa, said composition further comprising at least one mucoadhesive agent and/or one lipophilic or hydrophilic carrier and/or one permeation enhancer and/or, optionally, another pharmaceutically acceptable excipient.

Still another aspect of this invention is a method for treating a human female subject suffering from migraine or headache and/or nausea and vomiting associated with migraine or other diseases or conditions, said method comprising steps of contacting vaginal mucosa with a mucoadhesive composition or with an intravaginal device incorporated with said composition, said mucoadhesive composition comprising at least one anti-migraine and/or one anti-nausea drug.

Still yet another aspect of this invention is a mucoadhesive composition for delivery of anti-migraine and/or anti-nausea drugs said composition comprising, in dosage unit form, from 0.00001 to 45 mg/kg body weight, preferably from 0.001 to 15 mg/kg body weight and most preferably from 0.1 to 8 mg/kg/body weight of an anti-migraine drug selected from the group consisting of but not limited to ergotamine, dihydroergotamine, ergostine, butalbital, phenobarbital, acetaminophen, diclofenac sodium, ketoprofen, ketorolac, ibuprofen, piroxicam, naproxen, acetylsalicylic acid, flurbiprofen, tolfenamic acid, butorphanol, meperidine, methadone, sumatriptan, naratriptan, razatriptan, zolmitriptan, almotriptan, eletriptan, dexamethasone, hydrocortisone, isometheptene, chlorpromazine, diazepam, droperidol, valproic acid, gabapentin, topiramate, divalproex sodium, or an anti-nausea drug selected from the group consisting of metoclopramide, prochlorperazine, domperidone, ondansetron, tropisetron, dolasetron, nabilone, dronabinol, levonantradol, CP55940, SR 144528, aprepitant, cyclizine, and promethazine, BIBN-4096BS, SB-(+)-273779, each alone, in combination, or in combination with another therapeutically effective pharmaceutical agent and/or with a pharmaceutically acceptable excipient suitable for delivery of said drug to a human female subject through vaginal mucosa, said composition consisting essentially of a combination of an effective amount of said antimigraine and/or anti-nausea drug with at least a mucoadhesive agent promoting adhesion of the composition to the vaginal mucosa for delivery of the drug to and through the vaginal mucosa or with a combination comprising at least a mucoadhesive agent and/or a permeation enhancer and/or a lipophilic or hydrophilic carrier.

Yet another aspect of this invention is a vaginal device for vaginal delivery of an antimigraine and/or anti-nausea drug, wherein said device is a vaginal tampon, vaginal tampon-like foam, vaginal ring, vaginal pessary, vaginal sponge or vaginal tablet coated or partially coated with a layer(s) of an impermeable film, foam, foil or xerogel, or with an attached or removable cap, cup or strip, said layer incorporated with a composition comprising at least one anti-migraine and/or anti-nausea drug wherein said composition is formulated as a powder, cream, lotion, tablet, capsule, ointment, suppository, liposomal suspension, microemulsion, bioadhesive microparticles or microcapsules, bioadhesive nanoparticles or nanocapsules, solution, emulsion or gel.

Yet another aspect of the current invention is a mucoadhesive composition comprising an anti-migraine and/or anti-nausea drug in combination with an excipient selected from a lipophilic carrier such as semi-synthetic glyceride of saturated fatty acids, a hydrophilic carrier such as polyethylene glycol having an average molecular weight of 6000, polyethylene glycol having an average molecular weight of 1500, polyethylene glycol having an average molecular weight of 400, block polymers consisting of several repeating units in various sizes, co-polymers thereof or mixtures thereof, a muco-adhesive agent such as alginate, pectin, or a cellulose derivative, such as hydroxypropyl methylcellulose and a penetration enhancer such as a bile salt, organic solvent, ethoxydiglycol, interesterified stone oil, polyoxyethylene lauryl ether, polyoxyethylene monooleyl ether, polyoxyethylene nonylphenol, polyoxyethylene octylphenol ether, polyoxyethylene cholesterol ether, polyoxyethylene soya sterol ether, polyoxyethylene monooleate, polyoxyethylene dilaurate, polyoxyethylene dioleate, polyoxyethylene glyceryl laurate, polyoxyethylene glyceryl oleate, propylene glycol oleate, propylene glycol stearate, polyoxyethylene sorbitan monooleate, polyoxyethylene tristearate, polyoxyethylene hydrogenated castor oil, polyoxyethylene almond oil, polyoxyethylene apricot kernel oil, polyoxyethylene caprylic or capric glyceride, lauroyl macrogol glyceride, polyoxyethylene oleate or polyoxyethylene glyceryl stearate.

Still another aspect of the current invention is a mucoadhesive composition comprising a pharmaceutically acceptable excipient, wherein said excipient is a lipophilic or hydrophilic carrier, penetration enhancer and a mucoadhesive agent, wherein said lipophilic or hydrophilic carrier is present in amounts between about 60 to 90%, by weight, wherein said mucoadhesive agent is present in amounts between about 5 to 25%, by weight and wherein said penetration enhancer is present in amounts between about 5 to 20%, by weight.

Still another aspect of the current invention is a composition comprising about 75% lipophilic carrier (SUPPOCIRE®), about 10% hydroxypropyl methylcellulose (HPMC) and about 15% ethoxydiglycol (TRANSCUTOL®).

Still yet another aspect of the current invention is a tampon, a tampon-like foam or another vaginal device for delivering an anti-migraine or anti-nausea agent to the uterus or to the general circulation, said tampon, foam or device comprising a proximally placed cap or cup-shaped portion covered with a permanent or detachable cap or cup made of a fluid impermeable material incorporated with a mucoadhesive composition comprising an anti-migraine or anti-nausea drug.

Yet another aspect of the current invention is a tampon, tampon-like foam or another vaginal device comprising a proximally placed removable or permanently attached cup or cap coated with a fluid impermeable coating material further comprising a rim or strip containing a mucoadhesive composition containing a high concentration of an anti-migraine or anti-nausea drug.

Still yet another aspect of the current invention is a tampon, tampon-like foam or another vaginal device comprising a proximally placed fluid impermeable cap or cup encircled with a permanent or removable rim wherein said rim has fingers extending into the fornix areas around the cervix and wherein either the cap, cup or the tips of the fingers contain a mucoadhesive composition containing at least one anti-migraine or one anti-nausea drug.

Another aspect of the current invention is a tampon, tampon-like foam or another vaginal device completely or partially coated at its proximal end with a temperature-sensitive material, such as wax, that melts at the body temperature, said material comprising at least one anti-migraine or one anti-nausea drug suspended therein, wherein said tampon or device is further sheathed by one or several layers of fluid impermeable degradable or non-degradable thin, supple, non-porous material such as a plastic film, coated gauze, polyethylene, high density polyethylene, synthetic polymers or their combination with polysaccharides such as alginate, dextran, cellulose, collagen or proteins, such as albumin or gelatin, or polyhydroxy acids, such as polylactides, polyglycolides, polyethylene terephthalate, polybutyric acid, polyvaleric acid, polylactide-co-caprolactone, polyanhydrides, polyorthoesters, and blends and co-polymers thereof, or non-degradable polymers such as polyamides, polyethylene, polypropylene, polystyrene, polyvinyl chloride, polymethacrylic acid, and derivatives thereof, or any other suitable impermeable material that coats the device or surrounds the device like a skirt and opens like an umbrella when it comes in contact with the vaginal environment.

In yet another aspect of the current invention, a mucoadhesive composition comprising an anti-migraine or anti-nausea drug is formulated as a bioadhesive microparticle, cream, tablet, soft gel capsule, lotion, ointment, solution, gel or thermo-reversible sol-gel, all in a regular, controlled or sustained controlled release form and placed on, attached to or incorporated into an impermeable material coating of a vaginal device, tampon or tampon-like foam.

BRIEF DESCRIPTION OF THE DRAWINGS

FIG. 9 shows a tampon partially coated at its proximate end with a fluid impermeable coating wherein the proximal end of the tampon or a tampon-like foam is incorporated with a mucoadhesive composition comprising an anti-migraine or anti-nausea drug, said composition formulated as a tablet, suppository or gel capsule.

FIG. 10 shows a tampon or a tampon-like foam device coated with a fluid impermeable layer of material forming a cap with protruding fingers, said cap or only the fingers being incorporated with a mucoadhesive composition comprising an anti-migraine or anti-nausea drug.

FIG. 11 shows a partially coated tampon or a tampon-like foam device at its proximal end with a fluid impermeable layer of material forming a cap incorporating a scoop-shaped gel capsule comprising a mucoadhesive composition of the invention.

DEFINITIONS

Figure 1A:
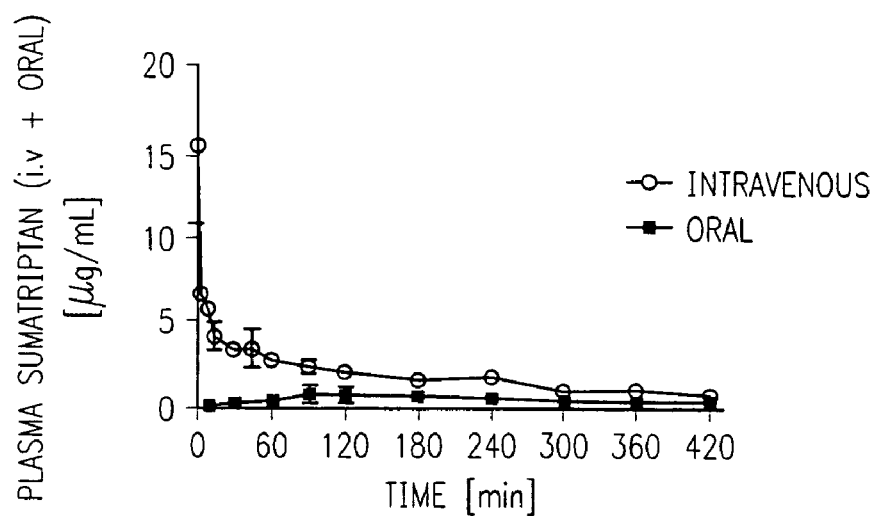
FIG. 1A is a graph illustrating pharmacokinetics of an anti-migraine drug sumatriptan in female white New Zealand rabbits following vaginal administration. Each animal received 0.7 mg of sumatriptan per kg body weight. Open circles (○) denote plasma concentration following intravenous injection, closed squares (■) represent corresponding to the drug plasma concentration after oral dosing. Results are presented as means±S.D.

As used herein:

Drug", "active compound", "chemical substance", "active ingredient" or "agent" means a therapeutically effective compound suitable for treatment, management, or control of migraine, nausea or other pathophysiological condition accompanied by nausea and/or vomiting.

"Pharmacological agent" or "therapeutic agent" means an anti-migraine drug, an anti-nausea drug, a mixture of both, or any other therapeutically effective pharmaceutically acceptable agent.

"Anti-migraine drug" means an agent involved in and suitable for treatment of migraine by administering a drug that reduces pathophysiological symptoms associated with migraine.

"Anti-nausea drug" or "antiemetic drug" means an agent which is suitable to partially or completely suppress nausea and/or vomiting typically associated with the migraine or any other disease or condition, such as infection, poisoning, chemotherapy, radiotherapy, pregnancy, surgery, or administration of drugs which cause nausea.

"Proximal end" means the end of the vaginal situated closest to the uterus and upper wall of the vagina when the tampon, tampon-like foam or another vaginal device is inserted therein.

"Distal end" means the end of the vaginal device situated away from the uterus and from the upper wall of the vagina when the tampon, tampon-like foam or another vaginal device is inserted into the vagina.

"Vaginal device" means a vaginal tampon, degradable or non-degradable vaginal foam, degradable or non-degradable tampon-like foam or any other vaginal device, such as pessary, sponge, tablet, ring or any other structure generally insertable into vagina.

"Pharmaceutical ingredient" or "excipient" means a pharmacologically inactive pharmaceutically acceptable compound added to a mucoadhesive composition of the invention. The ingredient or excipient does not have any pharmacological properties.

"Rapid delivery" means initial immediate rapid release and delivery of the drug from the mucoadhesive composition. The rapid delivery is typically followed by a time-dependent reduction in release of the drug from the mucoadhesive composition or device and delivery of the drug to the plasma.

"Continuous delivery" means continuous and uninterrupted release of the drug from the formulation or device and delivering such drug in a continuous manner. Continuous delivery may be preceded by the rapid delivery.

"Pulsed delivery" means a release and delivery of the drug in intermittent intervals. Such pulsed delivery may be provided, for example, by formulating the drug in individual layers interspaced with inactive layers of dissolvable coatings or by using different pharmaceutical ingredients.

"Chemotherapy" means a treatment of cancer using a chemical agent involved in treatment of disease by means of chemical substance or drug that exhibits cytostatic and/or cytotoxic effects on tumor cells.

"Interesterified stone oil" means a vegetable oil ethoxylated by replacing part of glycerol of the glycerides contained in vegetable oil by polyoxyethylene glycols of different lengths. Such replacement results in hydrophilic properties. Example of the interesterified stone oil is LABRAFIL®, particularly LABRAFIL® M1944 CS, commercially available from Gattefossé.

"Mucosa" or "mucosal tissue" means surface epithelial tissue that is accessible from the outside of the body without surgical procedures.

"Mucosal composition" or "mucoadhesive composition" means a composition which is suitable for administration to the mucosal tissue and adhere to such mucosal tissue.

"Permeation enhancer" means a compound that promotes transfer of an agent across a mucosal barrier and is increasing the mass transfer of the agent to, into, as well as through the mucosal epithelium.

DETAILED DESCRIPTION OF THE INVENTION

The present invention is based on the discovery that a vaginal device, such as a tampon, tampon-like foam or another type of vaginal device comprising impermeably sealed proximal end with a fluid impermeable coating material such as film, foam, foil, xerogel or another impermeable material attached permanently or removably to the vaginal device as a layer, layers, cap, cup, strip or strips incorporated with a mucoadhesive composition comprising a therapeutic and/or palliative amount of an anti-migraine and/or anti-nausea drug represents a suitable means for delivery of said drug to the uterus and/or to the general circulation for control and treatment of migraine and nausea.

The invention thus concerns a targeted delivery of anti-migraine and/or anti-nausea drugs to the uterus and/or to the general circulation using a vaginal device completely or at least partially coated with a layer or layers of the fluid impermeable coating material incorporated with or having attached to a mucoadhesive composition comprising an anti-migraine and/or anti-nausea drug, or a combination thereof. The vaginal device allows delivery of the an anti-migraine or anti-nausea drug directly to the uterus or to the general systemic circulation and permits a treatment of migraine or nausea with lower concentrations of anti-migraine or anti-nausea drugs than those needed for oral administration and thus provides for lower systemic concentration and fewer side effects.

Additionally, the invention concerns the discovery that when drugs are administered intra or transvaginally, preferably using an intravaginal tampon or tampon-like foam or another vaginal device for delivery of the anti-migraine or anti-nausea drug, uterus allows for preferential uptake of the drug into the uterus and into the general circulation thereby bypassing the first pass hepatic degradation and detoxification.

The current invention provides several previously unrecognized advantages. When a vaginal device coated with a fluid impermeable material at its proximal end additionally contains a layer containing the mucoadhesive composition comprising the drug, the released drug from the mucoadhesive composition is prevented from being absorbed into the distal porous non-coated portion of the device thereby making the whole dose of the drug available for transmucosal absorption. Additionally, when the mucoadhesive composition is incorporated into a layer of a temperature-sensitive carrier, such as, for example, wax, this carrier melts upon insertion into the vagina and releases the composition and the drug therefrom. Under these conditions, the mucoadhesive composition containing the entire dose of the drug is released and delivered to the upper vaginal wall closest to the uterus where, through its mucoadhesive properties, the composition adheres to said vaginal wall and the drug is transported through the vaginal wall to the uterus and/or to the general circulation. The invention thus permits a quantitatively more efficacious delivery of the drug wherein the substantially whole drug dose formulated as the mucoadhesive composition attached to or incorporated into the fluid impermeable coating or a layer is released and delivered.

Transmucosal vaginal delivery systems according to the invention offers a viable alternative to deliver anti-migraine and/or antiemetic (anti-nausea) drugs to a female subject suffering from migraine or other disease or conditions that result in headache, nausea or vomiting. In contrast to the oral route, administration of anti-migraine and/or anti-nausea drugs using vaginal drug delivery systems as described herein does not stimulate vomiting reflexes and, therefore, reduces migraine-associated vomiting. In addition, drugs delivered transmucosally through vaginal mucosa enter the systemic circulations system bypassing the first pass liver detoxification and degradation. Consequently, this route of administration is particularly advantageous for drugs, including anti-migraine and anti-nausea drugs, that undergo substantial first-pass hepatic metabolism which deactivates a large portion of the drug.

This type of drug delivery is particularly suitable for treatment of migraine because, typically, migraine is accompanied by severe headaches, nausea and vomiting. Nausea and vomiting prevent effective treatment of migraine by oral route because the recipient is usually not able to hold the drug in the stomach for long enough time to be absorbed and to achieve needed relief from the pain and nausea. Thus, the oral drug delivery for treatment of migraine and other conditions accompanied by nausea and vomiting is unpredictable and ineffective insofar as the actual delivered drug dose. Furthermore, women are generally accustomed, on a routine basis, to the insertion of a vaginal device such as a tampon for menstrual control and are expected to embrace this alternative route of delivery for therapeutic control of migraine condition without dramatic emotional distress.

The method of the invention provides a novel and more efficacious route of delivery of anti-migraine and/or anti-nausea drugs for treatment and control of the migraine condition as well as for control of nausea accompanying other conditions, such as drug-induced nausea, chemotherapy, radiotherapy, post-surgery nausea, pre-operative medication, PMS, menstruation, pregnancy, breast feeding and menopause, where administration of these drugs provides relief of similar symptoms in the female subject. The method avoids drug administration to the gastrointestinal tract of nauseated patients, protects the therapeutic agent from extensive hepatic first-pass metabolism, permits rapid or slow, continuous or pulsed delivery of the anti-migraine and/or anti-nausea drugs, and achieves therapeutically effective concentrations of such agents in the blood circulation with much smaller amounts of the drug.

The method for treatment and control of headache pain, nausea and vomiting comprises administration of a mucoadhesive composition containing a therapeutically effective amount of the appropriate anti-migraine or anti-nausea drug incorporated into a vaginal device of the invention before or after onset of migraine, before surgery, during menstrual period or pregnancy, or before or after headache, nausea and vomiting appear. The mucoadhesive composition attached to or incorporated into an impermeable layer covering at least a portion of the vaginal device is introduced into vagina attached to the vaginal device and brought into a close contact with a vaginal mucosa for direct absorption and transport through the mucosa into uterus and/or to the systemic circulation.

Administration of anti-migraine and/or anti-nausea drug via the vaginal route as described herein reduces the portion of the drug dose which would be eliminated by the liver during its first pass circulation in the blood system, which further enhances the drug's therapeutic effect.

I. A Method for Vaginal Delivery of Anti-Migraine or Anti-Nausea Drugs

A method for vaginal delivery of anti-migraine or anti-nausea drugs comprises preparation of a vaginal device at least partially coated with a layer or layers of fluid impermeable material that is incorporated with or having attached thereto a mucoadhesive composition comprising at least one anti-migraine or one anti-nausea drug. The mucoadhesive composition may contain a mixture of anti-migraine and anti-nausea drugs and may additionally and optionally also contain other therapeutic agents and/or other pharmaceutically acceptable excipients.

The mucoadhesive composition typically contains at least one mucoadhesive agent permitting the adhesion of the composition to the vaginal wall for a time needed for the active anti-migraine and/or anti-nausea drug to be absorbed through the vaginal mucosa into the uterus and/or general systemic circulation. Such delivery of the anti-migraine and/or anti-nausea drugs occurs without oral administration and thus eliminates therapy-induced vomiting typically occurring with oral administration of anti-migraine and/or anti-nausea drugs for treatment and control of headache, pain, nausea and vomiting. Headache, light sensitivity, pain, nausea and vomiting are primary symptoms associated with migraine but are also associated with other conditions or diseases and occur, for example, as a result of administration of chemotherapeutic drugs, following radiotherapy, before or after surgery, during menstrual period, pregnancy, breast-feeding, and menopause, among others.

A. Advantages of Vaginal Delivery

Existing therapeutic approaches used to control migraine symptoms and/or headache pain, nausea and vomiting mostly depend on oral, intravenous, nasal or rectal drug delivery systems. Unfortunately, drug administration via the gastrointestinal tract in migraine patients stimulates rather than eliminates vomiting and, consequently, results in inadequate treatment of these conditions. Alternatively, parenteral intramuscular or subcutaneous injections, nasal sprays, or insertion of rectal suppositories are employed to bypass problems and difficulties encountered with oral administration of these drugs to migraine patients. In this regard, injection methods usually require visit to a medical facility and assistance of a trained health care professional, whereas many patients find insertion of a rectal dosage form uncomfortable and/or emotionally unpleasant. Nasal delivery systems for migraine therapy have been only partially successful as the drug dose needed to achieve a relief from pain and nausea needs to be adjusted to consider first pass liver deactivation of the substantial amount of the drug and thus is efficacious only for drugs that are highly resistant to hepatic metabolism.

The vaginal route of delivery allows rapid or slow, continuous or pulsed delivery of drugs in a patient-controlled environment without the need to have access to a skilled health care professional in a doctor's office or hospital. Using the mucoadhesive composition and a vaginal device of the invention, an effective dose of a desired therapeutic agent can be delivered reproducibly to the systemic circulation while vomiting, which frequently occurs after oral drug administration in migraine patients, is prevented and eliminates parenteral injection with all its adverse effects and requirements. Furthermore, since the blood circulation into which the drugs are delivered through vaginal mucosa circumvents the liver first-pass circulation, the dose of the vaginally delivered drug is substantially smaller compared to the portion of the drug administered orally. In this regard, the vaginal delivery is many times more efficacious.

The invention, thus, concerns discovery of an improved delivery route of anti-migraine and anti-nausea drugs that overcomes the side effects and limitations observed during oral, parenteral, and nasal administration of these agents in subjects suffering from headaches or nausea. The invention utilized anatomic advantage of female subjects by focusing the delivery of drug therapy directly to the vaginal mucosa using a specifically formulated mucoadhesive composition attached to or incorporated into a fluid impermeable layer of a vaginal device.

The newly developed vaginal delivery strategy of anti-migraine and/or anti-nausea drugs according to the invention, therefore, represents an important improvement in the systemic delivery of these drugs and an important advancement of migraine therapy as well as the therapy of conditions leading to headache pain, nausea and vomiting associated with other diseases and conditions as described above.

B. Anti-Migraine and Anti-Nausea Drugs

Vaginal delivery of anti-migraine and/or anti-nausea drugs comprises formulating said anti-migraine or anti-nausea drugs into a mucoadhesive composition, incorporating said composition or attaching it to a layer, layers, strip, cup or cap of a fluid impermeable material coating at least a portion of a vaginal device and introducing said vaginal device into the vagina.

Examples of anti-migraine drugs suitable to be used in the current invention are therapeutic agents of type of ergot alkaloids and ergot alkaloids derivatives, antihistamines, barbiturates, non-steroidal anti-inflammatory agents, analgesics, serotonin antagonists, neurokinin-1 antagonists, cannabinoids, calcitonin gene-related peptide (CGRP) antagonists, steroids, sympathomimetics, tranquilizers and antiepileptics.

The anti-migraine drug useful for treatment of migraine according to this invention is selected from the group consisting of ergotamine, dihydroergotamine, ergostine, butalbital, phenobarbital, acetaminophen, diclofenac sodium, ketoprofen, ketorolac, ibuprofen, piroxicam, naproxen, acetylsalicylic acid, flurbiprofen, tolfenamic acid, butorphanol, meperidine, methadone, sumatriptan, naratriptan, razatriptan, zolmitriptan, almotriptan, eletriptan, dexamethasone, hydrocortisone, isometheptene, chlorpromazine, diazepam, droperidol, valproic acid, gabapentin, topiramate and divalproex sodium, among others.

A specific anti-nausea drug useful for treatment of nausea according to his invention is selected from the group consisting of metoclopramide, prochlorperazine, domperidone, ondansetron, tropisetron, dolasetron, nabilone, dronabinol, levonantradol, aprepitant, cyclizine and promethazine.

Each anti-migraine or anti-nausea drug may be formulated and delivered alone or in combination with each other or with another therapeutically effective agent or with a pharmaceutically acceptable excipient. Typically, the drug will be formulated in combination with at least one mucoadhesive agent, one carrier and one penetration agent.

The anti-migraine or anti-nausea drug is present in a dose sufficient to assert its therapeutic effect, typically from about 0.00001 to about 45 mg/kg body weight, preferably from 0.001 to 15 mg/kg body weight, most preferably from 0.1 to 8 mg/kg body weight.

C. Confirmation of Vaginal Delivery of Anti-Migraine and Anti-Nausea Drugs

Transmucosal delivery of anti-migraine and anti-nausea agents across the vaginal mucosa results in therapeutically useful systemic plasma concentrations. Consequently, vaginal administration represents a viable alternative to oral dosing for pharmacological agents with beneficial effects in the treatment of migraine and nausea, respectively.

To confirm feasibility of the method according to the invention, a series of in vivo pharmacokinetic studies was performed using female white New Zealand rabbits. Following administration of the anti-migraine drug sumatriptan and the anti-nausea drug metoclopramide as a solution intravenously by injection into the marginal ear vein or via the oral route using a rubber tubing inserted into the stomach as well as vaginally whereby the drug was incorporated into a suppository, plasma samples were withdrawn from the animal at predetermined time points and the drug concentration was quantitatively analyzed applying sensitive analytical methodologies.

Model-dependent pharmacokinetic analysis was further utilized to calculate relevant pharmacokinetic parameters such as maximum plasma concentration ($c_{max}$) time required to reach maximum plasma concentration ($t_{max}$), total exposure of the body to the drug extrapolated to infinity ($AUC_\infty$), and elimination half-life ($t_{1/2}$). All studies were repeated at least three times in different animals, and pharmacokinetic calculations were performed using WinNonlin 4.1.

Figure 1B:
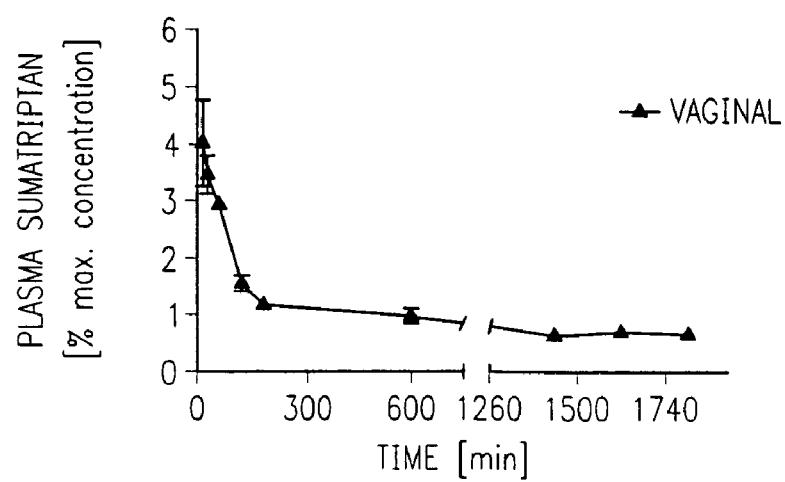
FIG. 1B shows systemic plasma concentrations of anti-migraine drug sumatriptan in female white New Zealand rabbits after vaginal insertion of a lipophilic vaginal delivery device. Each animal received 0.7 mg of sumatriptan per kg body weight and plasma concentrations were normalized to $c_{max}$ measured in similar experiments after oral administration of a dose-equivalent sumatriptan solution. Studies were performed in three different animals and results were presented as means±S.D.

The results for the anti-migraine drug sumatriptan are shown in FIGS. 1A and 1B.

FIG. 1A is a graph illustrating pharmacokinetics of an anti-migraine drug sumatriptan in female white New Zealand rabbits following vaginal administration. Each animal received 0.7 mg of sumatriptan per kg body weight administered as a solution. Open circles (○) denote plasma concentration following intravenous injection, whereas closed squares (■) represent corresponding drug concentration measured in the plasma after oral dosing of the drug solution. Experiments were performed in three different animals and results are presented as means±S.D. FIG. 1B shows systemic plasma concentrations of anti-migraine drug sumatriptan in female white New Zealand rabbits after vaginal insertion of a lipophilic delivery device. Each animal received 0.7 mg of sumatriptan per kg body weight and plasma concentrations were normalized to $c_{max}$ measured in similar experiments after oral administration of a dose-equivalent sumatriptan solution. Experiments were performed in three different animals and results were presented as means±S.D.

In these studies, a dose of 0.7 mg sumatriptan per kg body weight of the animal was used. For analytical purpose, the dose was supplemented with a trace amount of [$^3$H]sumatriptan, which was used to quantify plasma drug concentrations by liquid scintillation counting. Results are presented as means±SD.

FIG. 1A demonstrates that parenteral injection of the drug solution results almost immediately in high plasma concentrations that rapidly decrease with an apparent $t_{1/2}$ of 191±6 min. Therapeutically, the initial high concentrations with a $c_{max}$ of 15.4±4.5 µg/mL suggest fast onset of an effective relief of migraine headache and associated symptoms. However, since the drug is administered as a bolus into the blood stream, there is no constant supply that would support a longer duration of the action. Elimination of sumatriptan from the systemic circulation through metabolism and renal excretion are the predominant mechanisms by which the time of the anti-migraine effect is determined after injection.

In contrast, oral administration results in a very slow increase of systemic plasma concentrations of sumatriptan in the rabbit. This underlines kinetically the absorption phase required for the drug to physically move from the gastrointestinal tract across the epithelial barrier into the blood vessels of the submucosa. Physicochemical properties of the drug molecule, including ionization, lipophilicity, and hydrodynamic radius determine the rate of absorption.

Comparison of the two systemic profiles clearly suggests that oral administration of sumatriptan will result in a delayed anti-migraine effect as compared to parenteral injection. The $t_{max}$ values estimated for both i.v. and oral routes of administered drug indicate that the maximum effect of sumatriptan after oral administration is delayed by at least a factor of 100, which is therapeutically a dramatic disadvantage.

The overall exposure of the body to the same dose administered via the intravenous and the oral routes are significantly different as shown by the respective total area under the time/plasma concentration curve. The $AUC_\infty$ calculated for oral administration is 958±163 µg×min/mL and 10868±90 µg×min/mL (approximately 11 times higher) for parenteral administration, respectively. The apparent $t_{1/2}$ of 1210±163 minutes for oral administration is significantly longer than calculated from the intravenous data, which suggests that absorption rather than elimination becomes pharmacokinetically the rate-limiting process for this drug after oral administration.

To contrast the therapeutic potential of vaginal administration of anti-migraine drugs to the more frequently used oral route of administration, systemic plasma levels of sumatriptan measured after insertion of lipophilic vaginal device comprising sumatriptan composition were normalized to the maximum concentration attained after oral administration. Results are seen in FIG. 1B. In this representation, a straight line indicates similar kinetic processes involved in the absorption of this drug across the vaginal and oral mucosa, respectively. However, the early peak in this profile strongly suggests that vaginal administration of sumatriptan using said vaginal device as described in this application provide more rapid delivery of the drug into the systemic circulation that traditional oral administration. The calculated $t_{max}$ for vaginal administration is ~15 min, which implies that this delivery method may provide almost 6 times faster onset of anti-migraine efficacy when compared to the oral route. This therapeutic benefit could be compared with the previously described bolus effect after intravenous injection. The total body exposure to sumatriptan after an equivalent dose is <5% of that measured after oral administration. This requires incorporation of greater amounts of anti-migraine drugs into vaginal delivery device than for oral delivery methods due to incomplete absorption. The $AUC_\infty$ calculated for 0.7 mg/kg after vaginal delivery was 23.0±0.1 µg×min/mL.

Similar studies as performed with the anti-migraine drug sumatriptan were performed to demonstrate the value of vaginal delivery of anti-nausea drugs. Metoclopramide was selected as a model drug for this therapeutic class. Results are seen in FIGS. 2A and 2B.

Figure 2A:
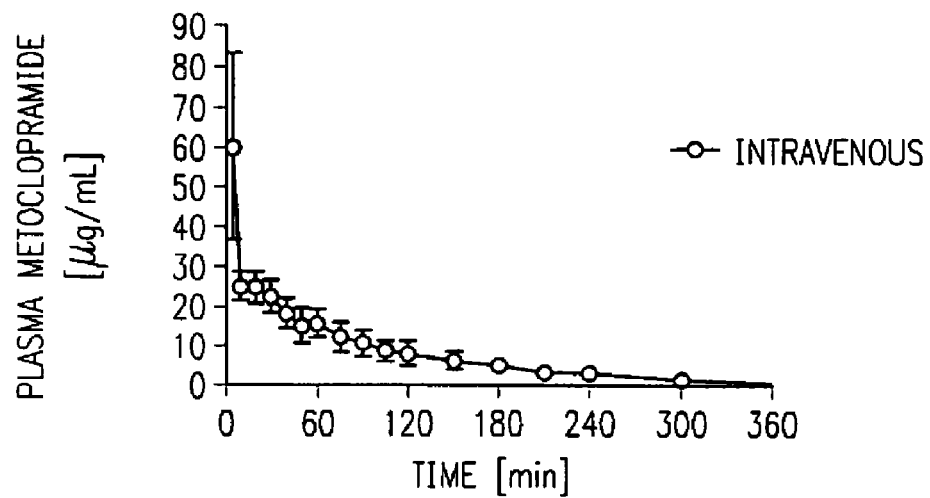
FIG. 2A shows an anti-nausea agent metoclopramide plasma concentrations in female white New Zealand rabbits after intravenous administration. Drug solution comprising 0.5 mg of metoclopramide was prepared in sterile saline (0.9%; w/w) and injected into the systemic circulation through the marginal ear vein. Plasma samples were collected for six hours and analyzed for the drug using HPLC. Results are presented as means plasma±SEM (n=4).
Figure 2B:
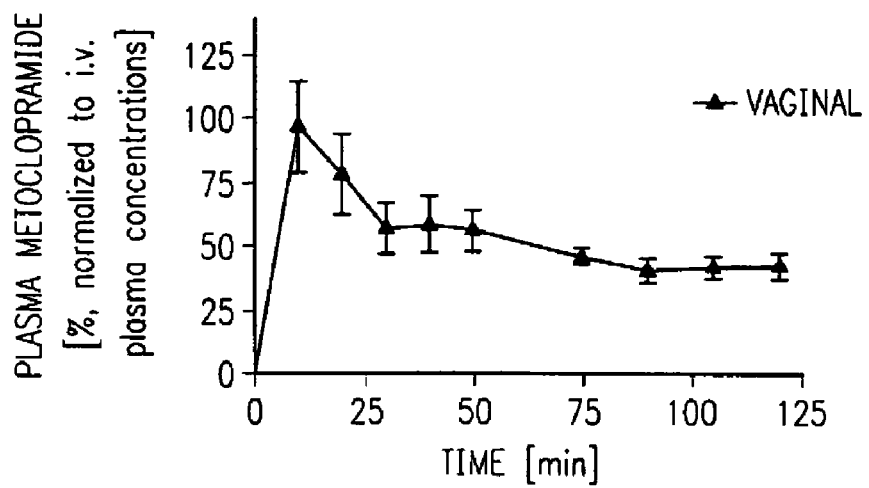
FIG. 2B shows normalized metoclopramide plasma concentrations in white female New Zealand rabbits after vaginal administration. Plasma samples were analyzed for the drug using a selective HPLC method and normalized to metoclopramide concentrations measured at the same time points as those used for intravenous injection. Experiments were performed in three individual animals and results are presented as mean±SEM.

FIG. 2A shows an anti-nausea agent metoclopramide plasma concentrations in female white New Zealand rabbits after intravenous administration. Drug solution of 0.5 mg was prepared in sterile saline (0.9%; w/w) and injected into the systemic circulation through the marginal ear vein. Plasma samples were collected for six hours and analyzed for the drug using HPLC. Results are presented as means plasma+ SEM (n=4) FIG. 2B shows normalized metoclopramide plasma concentrations in white female New Zealand rabbits after vaginal administration. Plasma samples were analyzed for the drug using a selective HPLC method and normalized to metoclopramide concentrations measured at the same time points after intravenous injection. Experiments were performed in three individual animals and results are presented as mean±SEM.

Three female white New Zealand rabbits were dosed at 0.05-0.1 mg/kg body weight intravenously, orally, and vaginally. Blood samples were removed at various time points, and plasma concentrations were quantified using a selective HPLC method described in *Int. J. Clin. Pharmacol. Ther.*, 40: 169-174 (2002). Model-dependent pharmacokinetic parameters were calculated from time/plasma concentration data using WinNonlin 4.1.

Intravenous injection of a metoclopramide solution prepared in 0.9% saline immediately reaches average plasma concentrations around 60 ng/mL (FIG. 2A). First-order distribution and elimination phases result in a monophasic decline of plasma concentrations with an apparent $t_{1/2}$ of 84±38 min. Total body exposure as measured by the $AUC_\infty$ was 3845±1415 ng×min/mL. Oral administration of the same dose resulted in peak plasma concentration that were on average 30-fold lower than measured after parenteral administration (data not shown) This implied that the transfer of this anti-nausea drug from the gastrointestinal tract into the systemic circulation is inefficient. Considering the additional complication that patients who are vomiting experience great difficulties, in general, to swallow oral dosage forms, it becomes apparent that oral delivery of anti-nausea drugs such as metoclopramide appears therapeutically undesirable. However, inclusion of this drug into a vaginal delivery device consisting of a lipophilic base such as SUPPOCIRE AS2, the mucoadhesive hydroxypropyl methylcellulose, and the permeation enhancer ethoxydiglycol provides a unique opportunity to bypass the irritated gastrointestinal tract in female patents and deliver therapeutically sufficient amounts into the systemic circulation.

Results of the vaginally administered metoclopramide depicted in FIG. 2B demonstrate that plasma levels of metoclopramide delivered vaginally using a device such as described above are close to the respective drug levels measured after intravenous injection. The profile shown in FIG. 2B was generated by normalizing the actual plasma levels measured for metoclopramide after vaginal administration to the time-equivalent levels after parenteral administration. Consequently, the initial concentrations appearing after 10 minutes following vaginal dosing are equivalent within intersubject variability to plasma levels after parenteral administration. Therapeutically, this may offer great benefit to the patient suffering from vomiting without the requirement to inject the drug.

The above described studies clearly demonstrate feasibility and benefits of vaginally delivered anti-migraine and anti-nausea drugs. Clearly, such vaginal delivery provides much larger dosage of the drug delivered more rapidly and for longer time than that achieved by oral administration. Advantages of the vaginal delivery of anti-migraine and anti-nausea drugs compared to requirements, inconveniences and invasiveness of the intravenous administration are obvious.

II. Devices for Vaginal Delivery of Anti-Migraine and Anti-Nausea Drugs

The vaginal device of the invention, such as a tampon, foam, tampon-like foam, sponge, pessary or ring provides an improvement against previously described devices. In particular, the device of the invention, which is preferably the vaginal tampon or a degradable or non-degradable tampon-like foam is coated completely or, preferably, only partly at its proximal end with a layer of a fluid impermeable material.

The fluid impermeable material may be applied to the device as one layer or several layers interspaced with a layer or layers of different material, it may form a cap or cup covering a proximal portion of the tampon or a strip or rim of a fluid impermeable material encircling the tampon. Since the vaginal tampon or vaginal foam is made of porous material, usually a cotton or polymer, the fluid impermeable material covering at least a proximal portion, typically the proximal end of the tampon, separates the porous material from the material coated with the impermeable layer and sequesters the proximal portion of such porous material within the fluid impermeable coating. The fluid impermeable coating, whether the layer, layers, strip, strips, cap or cup, is incorporated with a mucoadhesive composition or such composition is attached to such fluid impermeable coating by various means.

The coating of the entire device prevents the absorption of the mucoadhesive composition into the porous portion of the device. The partial coating of the device permits sequestration of the drug to a smaller area and prevents the absorption of the mucoadhesive composition into the porous portion of the device. Thus, the loss of the drug due to reabsorption into the porous portion of the device is either eliminated or substantially decreased. Additionally, since the mucoadhesive composition comprising the anti-migraine or anti-nausea drug is sequestered within the fluid impermeable coating applied to the proximal end of the device, it is preferentially released from the device into the vicinity of uterus where the mucosal epithelia is more apt to drug absorption. The drug is therefore delivered more quantitatively to the vaginal mucosa to which it adheres due to the presence of the mucosal agent and is transported through the mucosa to the uterus and/or to the general systemic circulation due to the presence of the sorption promoter and/or penetration enhancer. The lipophilic or hydrophilic carrier additionally modifies the drug affinity to the mucosal surface and enhances the drug surface exposure.

A. Coated Vaginal Devices

The vaginal device of the invention is a vaginal tampon, degradable or non-degradable vaginal tampon-like shaped foam, vaginal foam, vaginal sponge, vaginal ring or vaginal pessary, all coated or at least partially coated with an impermeable layer of coating separating the body of the device from the mucosal composition incorporated into or attached to said coating. The most preferred embodiment is a vaginal tampon or the tampon-like shaped foam.

1. Vaginal Tampon

One preferred embodiment for vaginal drug delivery is the vaginal tampon. The vaginal tampon is typically a commercially available vaginal tampon that is coated, according to the invention, in its upper proximal portion, typically to about one third or one half, that is a portion coming in contact with the vaginal wall. The proximal end of the tampon is coated with a fluid impermeable coating forming a layer, layers, cap, cup or strip around the upper proximal top portion of the tampon or attached to the tampon as a fluid impermeable layer, cap or cup or strip prepared separately. However, the whole tampon may also be coated with the fluid impermeable coating, if desirable and the composition is then attached to the whole, to the proximate part, or to the tip of the tampon.

2. Vaginal Foam

Another preferred embodiment is a tampon-like shaped vaginal foam that may be fully or partially degradable in the vagina or it may be non-degradable. However, the foam may also be shaped differently than a tampon-like structure.

The foam used as a vaginal device is preformed into a specific shape of a solid structure or a semi-solid or liquid preparation. The latter two may be used as a receptacle for the mucoadhesive composition which forms a foam layer, strip, cup or cap coating into which the composition may be conveniently incorporated.

The vaginal foams, whether degradable or non-degradable and whether used as a vaginal device or a coating therefore, are prepared by processes known in the art that introduce porosity in a polymer matrix, namely by lyophilization, aeration, freeze drying, hydrocarbon templating, salt or particulate leaching, gel or solvent casting, gas expansion, sintering, polymerization of high internal phase emulsions, and free form fabrication techniques such as three-dimensional polymer printing. The most preferred process to fabricate foams is lyophilization, which is described in detail in the copending application Ser. No. 10/600,849 filed Jun. 30, 2003.

Lyophilized foams are open cell, high-surface-area, biodegradable or non-degradable constructs that can be manufactured from a variety of polymers, preferably from hydrophilic polymers. The foam materials are characterized by controlled chemical and physical properties that can be tailored according to their intended application. Tuneable properties include hydrophilicity, rate of fluid absorption, degradation profile and dissolution rate, a measure of which is the time needed to complete dissolution of the foam.

Typically, the lyophilized foam is prepared by dissolving an appropriate polymer, preferably a hydrophilic polymer, or a mixture thereof, serving as a substrate material, as listed below, in an amount needed to prepare solution from 1 to 10% (w/w) in an aqueous or non-aqueous solvent, such as methanol, ethanol, glycerine, methylene, chloride, propylene glycol, propylene carbonate, glycofurol, cetyl alcohol, difluroethane and isopropyl alcohol, preferably a purified water. Alternatively, polymeric solutions with the drug and additives may be prepared in acetic acid, cyclohexane, acetonitrile, tert-butanol, ethanol, and isopropanol or in mixtures of aqueous and non-aqueous solvents.

Substrate materials for preparation of foam compositions of the invention are hydrophobic or, preferably, hydrophilic polymers. These polymers may be used singly or in combination with each other. They may be used in variable concentrations and ratios to each other when in admixture of two or several polymers.

Non-exclusive list of substrate polymers comprises cellulose and cellulose derivatives, microcrystalline cellulose, polyacrylic acid, polyethylene glycol, polypropylene glycol, divinyl glycol, polyethylene oxide, polypropylene oxide. Other possible polymers include the cellulose derivatives such as carboxymethyl cellulose, hydroxyethyl cellulose, polylactide, polyglycolide, polymethacrylic acid, poly-γ-benzyl-L-glutamate, polypropylene fumarate, poly-ϵ-caprolactone, poly-butylene terephthalate, polyvinyl alcohol, polyvinyl ether, poly-1-vinyl-2-pyrrolidinone, 2,5-dimethyl-1,5-hexadiene, divinyl benzene, polystyrene-divinyl benzene, polyanhydrides such as poly-bis-p-carboxy-phenoxypropane-co-sebacic acid, polyhydroxyalkanoates such as poly-β-hydroxybutyrate or poly-β-butyrolactone, and alkyl-substituted silica gel such as tetraethylorthosilicate and dimethyldiethoxysilane.

Examples of hydrophilic polymers suitable for a foam manufacture include hydroxypropyl methylcellulose (HPMC), sodium carboxymethylcellulose, polyethylene glycol (PEG), alginic acid, alginic acid sodium salt, pectin, gelatin, collagen, polyvinyl pyrrolidone, poloxamer, acrylic-acid based polymers, such as carbopol, noveon, polyurethanes, polyvinyl alcohol, chitosan, hydroxypropyl cellulose, polyethylene oxide, fibronectin, hyaluronic acid, polysaccharide gums such as karaya gum, polyacrylamide, polycarbophil, dextran, xanthan gum, polyacrylamide, polyacrylamide, crosslinked polymethyl vinyl ether-co-maleic anhydride, commercially available as Gentrez™, gelatin, corn starch and mixtures thereof.

Examples of hydrophobic polymers suitable for formation of the foam are, among others, polypropylene oxide, polyamides, polystyrene, and polymethacrylic acid.

Tampon-like vaginal foams that undergo degradation in the vagina into smaller units or polymers by various mechanisms are classified as degradable foam. This type of the foam is preferred as long as their degradation is controlled and coincides with or exceeds the time needed for a complete release of the drug from the coating attached to the degradable vaginal foam.

Non-degradable vaginal foams are the foams resisting a degradation of the three-dimensional structure. Representative but not limiting examples of non-biodegradable polymers that may be used exclusively, or in alternative that may be also coated with biodegradable polymeric foams, include polyamides, polyethylene, polypropylene, polystyrene, polyvinyl chloride, polymethacrylic acid, and derivatives thereof alone or as co-polymeric mixtures thereof.

Both degradable or non-degradable foams may be prepared in a range of sizes and a variety of shapes suitable for use as a vaginal device or the coating thereof, including foam pillows, tubes, cylinders, spheres, tablets or rings (devices) or films, sheets or beads or any other desirable shape (coating) using an appropriate processes known in the art that introduce porosity in a polymer matrix.

The foam as a vaginal device is preformed into a device such as a tampon, tampon-like cylinder, strip, pad, pillow, tube, sphere, tablet or ring or any other shape as might be desirable or it may be applied as a film, sheet or beads, as a coating to a surface of a more complex vaginal device made of a different material, such as, for example, a conventional vaginal tampon, tampon-like device, pessary, ring, strip, pad, pillow, sheet, tube, sphere or tablet covered by said coating foam. In this configuration the foam is applied as a receptacle for the mucoadhesive composition as described in greater detail in the coating section below.

3. Vaginal Sponge

Another example of the tampon-like device is the vaginal sponge. The mucosal composition comprising a desired anti-migraine or anti-nausea drug can be incorporated into a fluid impermeable silicone matrix which is coated onto a cylindrical drug-free polyurethane vaginal sponge.

4. Vaginal Ring

Another example of a suitable controlled release drug delivery system for the present invention is the vaginal ring. Vaginal rings usually consist of an inert elastomer ring coated by another layer of elastomer containing the drug to be delivered. The rings can be easily inserted, left in place for the desired period of time, up to 7 days, then removed by the user. The ring may be solid or hollow containing the anti-migraine and/or anti-nausea drug and it may be coated with a porous material releasing the drug therefrom. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

5. Other Vaginal Devices

Vaginal pessaries, vaginal cylinders, vaginal tablets, vaginal capsules, vaginal pads, vaginal patches, vaginal suppositories or vaginal tubes are other examples of drug delivery systems which can be used in the present invention. These systems have been previously used for delivery of vaginal contraceptives, and have been described extensively in the literature.

These other types of vaginal devices are similarly coated on the side or on the end facing the uterus with the fluid impermeable coating. For example the pessary or ring can be coated on the side facing the uterus with the other side remaining non-coated, sponge or pad may be coated at the portion closest to the uterus while the other side may be porous and adsorbent for, for example, the menstrual blood.

The vaginal device is provided in dry or wet form or may be wetted prior to insertion.

6. Detailed Description of Figures

Various embodiments of the vaginal device of the invention vis-a-vis the female reproductive system are illustrated in FIGS. 3-15 using a vaginal tampon or foam as a non-limiting example.

Figure 3:
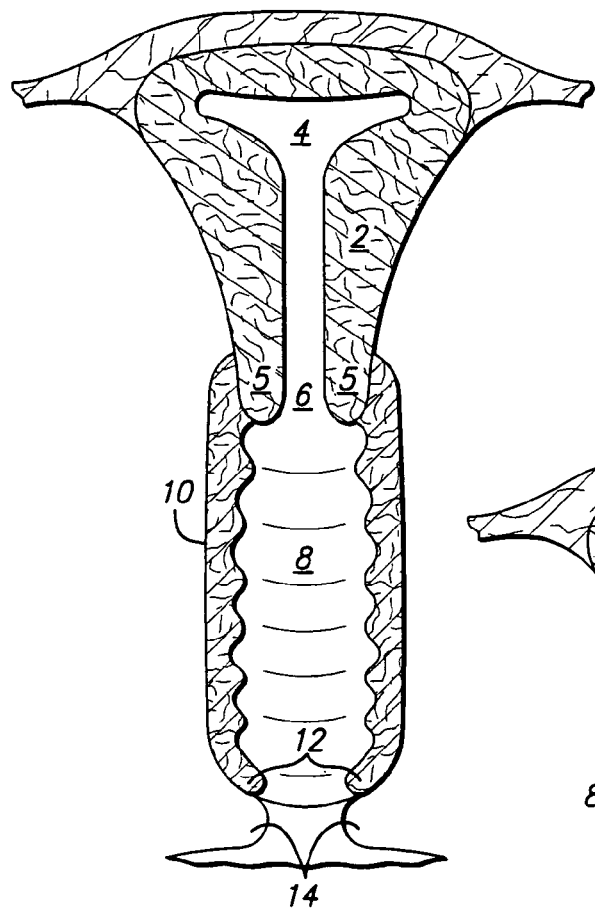
FIG. 3 is a cross-sectional representation of a portion of the female reproductive organs including the uterus and vagina in the upright orientation.
Figure 4:
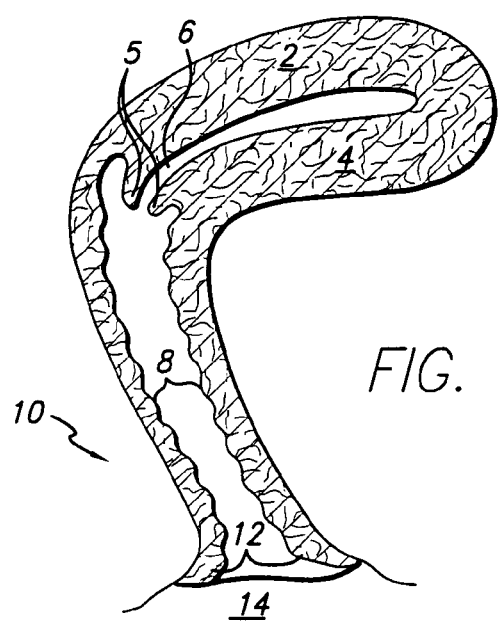
FIG. 4 is a cross-sectional side view representation of a portion of the female reproductive organs including the uterus and vagina.

FIG. 3 is a cross-sectional representation of a portion of the female reproductive organs including the uterus and the vagina in the upright orientation. FIG. 4 is a cross-sectional side view representation thereof. The uterus 2 is a muscular organ enclosing the womb 4, and opening at the cervix 5 via the cervical canal or cervical os 6. The vagina 8 is defined by a muscular tube 10 leading from the labia minora 12 and labia majora 14 to the cervix 5. The local vasculature associated with the walls of the vagina 8 communicate with the uterine muscle vascular and lymphatic systems.

Figure 5:
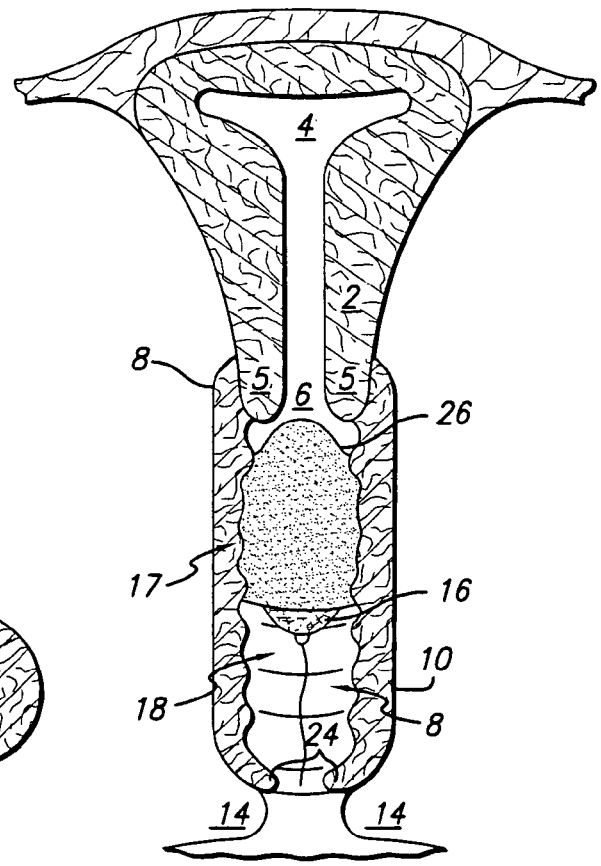
FIG. 5 shows placement of a vaginal tampon or a tampon-like foam device covered with a fluid impermeable cap comprising a mucoadhesive composition containing an anti-migraine or anti-nausea drug incorporated therein or attached thereto.

FIG. 5 shows placement of a vaginal device 16 in the vagina 8. The vaginal device, represented by a vaginal tampon, is coated in its upper proximal portion with a fluid impermeable film coating 17 incorporated with a mucoadhesive composition. Non-coated porous portion 18 of the tampon is seen at the distal end of the tampon. Due to its mucoadhesive properties, the drug or the composition is released from the coating into vagina, adheres to the vaginal mucosa and is transported to the uterus by way of the vaginal blood vascular and lymphatic systems. Physiologically, this concept has been documented and confirmed in animal experiments reported, for example, in the patent U.S. Pat. No. 6,086,909, hereby incorporated by reference.

FIGS. 6-13 depict various embodiments of vaginal devices which can be used to deliver the an anti-migraine or anti-nausea drugs to the uterus or to the general circulation for treatment of migraine and nausea according to the invention.

Figure 6:
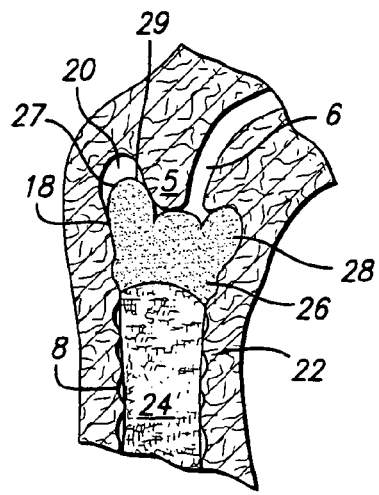
FIG. 6 is a cross-sectional side view representation of the vaginal area adjacent the cervix showing placement of one embodiment of a vaginal tampon or a tampon-like foam coated with a layer or layers of an impermeable material incorporated with a mucoadhesive composition containing an anti-migraine or anti-nausea drug.

FIG. 6 is a cross-sectional representation of the vaginal area, adjacent the cervix 5, with a fluid impermeable layer attached to the tampon device according to the invention. The tampon device 22 comprises an absorbent cylindrical tampon comprised of non-coated fibrous material 24, for example cotton, at a distal end as well as a coated portion at its proximal end 26 with an annularly positioned a fluid impermeable layer in a shape of a cup 29 comprising a composition 28 incorporated into said cup. The proximal end of the tampon device 27 is placed against the upper epithelium 18 of the vagina 8 and posterior fornix 20 for drug delivery through the vaginal mucosa with which the composition 28 is in contact. The composition 28 can be incorporated into an impermeable layer coating material, but may also be a powder, melted suppository, foam, paste, or gel composed of suitable delivery components emplaced into the cavity inside the cup.

Figure 7:
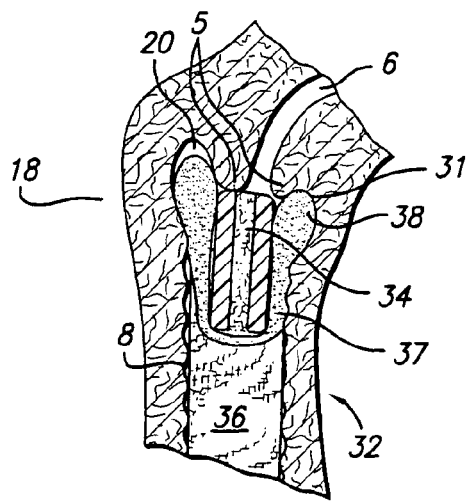
FIG. 7 shows placement of a vaginal tampon or a tampon-like foam device covered with a layer of impermeable material insulating the device from a material containing a mucoadhesive composition wherein the impermeable material forms a protective skirt-like around the proximal medicated portion of the device placed into a close proximity of the vaginal mucosa.

FIG. 7 is a cross-sectional representation of the vaginal area adjacent the cervix 5 with a tampon device described in the FIG. 6. As seen in the FIG. 7, in the cross section, the cup 31 may contain the mucoadhesive composition 37 incorporated into the cup's wall or such composition may be inserted or placed inside of the cup's inner cavity as a capsule, powder, gel, cream or any other suitable configuration. The fluid impermeable cup 31 is pushed against and is in a close proximity to the vaginal mucosa wherein the drug is released. In the shown embodiment, tampon device 32 includes a non-porous tube 34 which communicates with the cervical os 6 for delivery of the an anti-migraine or anti-nausea drug from, for example, capsule inserted into the cup inner cavity. Such tube is, of course, an optional feature in this embodiment.

Figure 8:
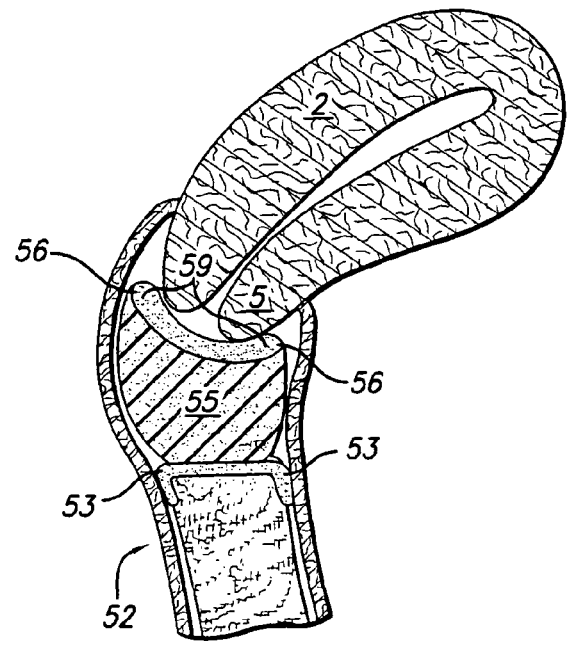
FIG. 8 shows an alternate embodiment of the tampon or a tampon-like foam device coated with a fluid impermeable coating wherein a mucoadhesive composition is incorporated into the porous foam cap separated from the body of the tampon by the impermeable layer wherein the foam material used for the device is different from the foam device material used for formation of the foam cup.

FIG. 8 is a cross-sectional representation of the vaginal area adjacent the cervix 5 which shows an alternate placement of the tampon-like foam device forming a cap coated with a fluid impermeable coating wherein the composition is incorporated into the porous foam cap 55 impermeably separated from the body of the tampon with the impermeable layer 53. The entire cap 55 or only an upper proximal portion 56 thereof may be incorporated with the mucoadhesive composition or coated with the composition of the invention.

FIG. 9 is a cross-sectional representation of the vaginal area adjacent the cervix 5 showing a tampon 62 coated with a fluid impermeable coating 53 with the composition, such as a tablet, capsule, a dissolvable suppository or gel capsule 67 placed within the coating or incorporated into the coating immediately adjacent to the vagina and being available for release to the vagina.

FIG. 10 is a cross-sectional representation of the vaginal area adjacent the cervix 5 with the tampon device 72 including a fluid impermeable cap having a protruding fingers 76 which extend into the fornix areas 20 around the cervix 5. The tips of the fingers 76 contain high concentrations of the mucoadhesive composition 75 which may be delivered to more remote areas of vaginal surface.

FIG. 11 illustrates a tampon device 80 having attached thereto a fluid impermeable removable cap 88 incorporating a scoop-shaped gel capsule 85 comprising a pharmaceutical composition of the invention. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver the mucoadhesive composition to the vaginal wall along the entire length of the scoop-shaped porous foam section 87.

Generally, the tampon device coated with the fluid impermeable coating layer, strip, cup or cap is placed in contact with the inner wall of the vaginal mucosa and the therapeutically inactive excipients present in the mucoadhesive composition, namely a lipophilic or hydrophilic carrier, penetration enhancer and mucoadhesive compound act to facilitate the release and adsorption of the drug into the local vasculature. This results in a substantially higher concentration of the drug being delivered to the uterus and/or to the systemic circulation.

Embodiments of the invention seen in FIGS. 3-11 may include tampon-like devices of a standard length, or may be longer or shorter than standard tampons to facilitate positioning the tampon device closer to or in contact with the vaginal wall or with the cervix, depending on the shape of the device.

It will be readily apparent to a person skilled in the art that any characterization of the tampon device as having that or another shape is only an approximate description of the vaginal device according to this invention and the device of any shape, form or type that brings the mucoadhesive composition in contact with the adjacent vaginal wall epithelium, and all shapes which conform to the vaginal epithelium and external cervical surfaces are intended to be included within the scope of this invention. Moreover, no term used herein restricts the invention to the use of such devices.

B. Attachment or Incorporation of Mucoadhesive Compositions to the Vaginal Device The mucoadhesive compositions comprising an anti-nausea or anti-migraine drug and their components are described separately in the following section. This section deals only with the attachment or incorporation of these compositions into the impermeable layers, caps, cups, or strips coating or attached to the vaginal device.

The mucoadhesive composition comprising an anti-migraine or anti-nausea drug is attached or incorporated into said fluid impermeable coating or into the cap, cup or strip. The mucoadhesive composition additionally typically comprises a mucoadhesive agent, and/or a lipophilic or hydrophilic carrier and/or a penetration enhancer and/or sorption promoter. The composition can be a paste, powder, solution, emulsion, cream, or gel having a sufficient thickness to maintain prolonged vaginal epithelium contact. Alternatively, the mucoadhesive composition can be formulated as an impermeable coating, a suppository, a sponge, a tablet, a capsule or other absorbent material impregnated with a solution, lotion, or suspension of bioadhesive particles, for example. Any form of drug delivery system which will effectively deliver the agent to the vaginal endothelium is intended to be included within the scope of this invention.

Mucoadhesive compositions are either incorporated into, placed on or in, or attached to the impermeable layer, cap, cup or strip that act as their delivery vehicles or structures. The drug-containing composition can be incorporated into these structures before their attachment to the impermeable layer or before their attachment to the vaginal device or it can be incorporated by partially or totally coating of the vaginal device or a surface of a prefabricated vaginal tampon or polymeric vaginal foam or other vaginal device.

If the vaginal device coated with a fluid impermeable layer is used, there are numerous methods by which a composition can be incorporated into the device. For example, the composition can be incorporated into a coating layer or one of the coating layers, it can be incorporated into the cap covering the tampon, it can be incorporated into a fluid impermeable cup surrounding the proximal portion of the tampon, or into a tablet, gel-like capsule or bioadhesive reservoir placed into or attached to the layer, cap, cup or strip coating near the proximate end of the vaginal device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the fibers. The drug can also be dissolved in a coating material which is applied to the proximate end or the tip of the device and/or placed around the fluid impermeable coating attached to the tampon. Alternatively, the drug can be incorporated into an insertable suppository which is placed in association with the tip of the tampon or in or on the cap either attached or the tampon device or removable and attached or administered separately.

One route to deposit the mucoadhesive composition is to spray the device with an impermeable layer coating material containing a concentrated drug solution or in alternative to spray the device first with the impermeable coating and then to spray or add the second layer containing the drug or attach the pre-formed cap, cup or strip containing the mucoadhesive composition. Suitable processes to coat the vaginal device are similar to processes used for applying coatings to pills.

Alternatively, the composition can be incorporated into the impermeable layer or cup, cap or strip by emulsion coating where water-in-oil or oil-in-water emulsions prepared in polymer solution is forced through a prefabricated foam scaffold by applying vacuum. After solvent evaporation, a polymer film containing the drug is incorporated into the structural layer, cap, cup or strip. Processing parameters of this emulsion coating are known to the skilled in the art and any type of process, additives and equipment required to optimize stability and release of the anti-migraine and anti-nausea drugs from within these structure are intended to be within the scope of this invention.

C. Fluid Impermeable Layer

The fluid impermeable material is applied to the device as a layer, layers, cap, cup or strip incorporated with the mucoadhesive composition that acts as continuous drug depots, and depending on the formulation, providing a continuous and uninterrupted delivery of the drug to the vaginal mucosa over a long period of time.

The vaginal device is coated with the fluid impermeable layer either completely or partially. Preferably the impermeable layer coating is applied to the proximal end of the device. Such coating may be a temperature-sensitive material, such as wax, that melts at the body temperature, or one or several layers of fluid impermeable degradable or non-degradable thin, supple, non-porous material such as a plastic film, coated gauze, polyethylene, high density polyethylene, synthetic polymers or their combination with polysaccharides such as alginate, dextran, cellulose, collagen or proteins, such as albumin or gelatin, or polyhydroxy acids, such as polylactides, polyglycolides, polyethylene terephthalate, polybutyric acid, polyvaleric acid, polylactide-co-caprolactone, polyanhydrides, polyorthoesters, and blends and co-polymers thereof, or non-degradable polymers such as polyamides, polyethylene, polypropylene, polystyrene, polyvinyl chloride, polymethacrylic acid, and derivatives thereof, or any other suitable fluid impermeable material that coats at least a portion of the device with a layer, strip or several layers or strips, covers the portion of the device with a fluid impermeable cup or cap, or surrounds the device with a fluid impermeable coating like a skirt or that opens like an umbrella when it comes in contact with the vaginal environment.

In one embodiment, the impermeable layer is itself incorporated with the mucoadhesive composition. In other embodiments, the impermeable layer is used only as a separating barrier for sequestration of the non-coated part of the vaginal device from the coating or from the structure containing the mucoadhesive composition. In both alternatives, the layer or permanently attached or removable cup, cap or strip or another layer is separated from the non-coated part of the vaginal device. Preferably only the coated part of the device is in contact with the epithelial tissue.

The impermeable layer coating may be applied to the vaginal device as a continuous film, foam, foil or sheet. Additionally, such impermeable layer coating may be further coated with another layer of film, foil, foam, sheet, beads, microcapsules, nanocapsules and any such formulation that can conveniently contain the mucoadhesive composition of the invention and release such composition in timely manner when placed in contact with the vaginal mucosa.

Biodegradable polymers suitable for preparation of these films, foils, foams or sheets are preferably designed to allow drug release by bulk or surface erosion and include natural and synthetic polymers alone or in combination with representative but not limiting examples of polysaccharides such as alginate, dextran, cellulose, collagen, and chemical derivatives thereof, proteins such as albumin and gelatin and copolymers and blends thereof, polyhydroxy acids such as polylactides, polyglycolides and co-polymers thereof, polyethylene terephthalate, polybutyric acid, polyvaleric acid, polylactide-co-caprolactone, polyanhydrides, polyorthoesters, and blends and co-polymers thereof.

Physical and chemical properties of films, foams, foils or sheets of the invention can be tailored to optimize their intended use, which is achieved by controlling the rate of release of the anti-migraine and anti-nausea drugs incorporated therein. Drug release from the delivery device can occur by diffusion or erosion, or by a combination of both, leading to immediate and controlled, rapid, slow, continuous or pulsed delivery of the drug to and through the vaginal epithelia.

The rate of drug release depends on physicochemical properties of the drug, on the composition of the film, foil, foam or sheet and also on the surrounding media at the site of administration.

The release of drug from the tampon device should be timed to provide proper uterine concentration of the drug over a typical length of use of a tampon device, usually 1-8 hours. However, when the degradable devices, such as, for example, vaginal foams or sponges are used, the release of the drug can be timed to coincide with he foam degradation time.

The above approach keeps the agent present in the composition from being absorbed into the tampon and thus becoming unavailable for delivery. When the fluid impermeable barrier is present the composition absorbs into the vaginal mucosa quantitatively instead of being only partially delivered to the vaginal mucosa and partially absorbed into the tampon. This cap can also be used as a repository for a tablet, gel capsule or the pellet containing the composition of the invention containing the appropriate an anti-migraine or anti-nausea drug.

III. Mucoadhesive Compositions

A mucoadhesive composition of the invention for transmucosal delivery of anti-migraine or anti-nausea drugs consists typically of four essential components. These components are an anti-migraine and/or anti-nausea drug that achieves a therapeutically desired effect, a mucoadhesive agent that provides close contact of the composition with the vaginal epithelium, a lipophilic or hydrophilic carrier that assures enhances surface exposure of the drug to the vaginal mucosa, and a permeation enhancer that facilitates transfer of the drug across the vaginal epithelial barrier into the submucosa tissue and systemic blood circulation.

The mucoadhesive composition is typically formulated in therapeutic unit dosage forms and contains an anti-migraine or an anti-nausea drug selected from those already described in section I. A. The composition typically contains from 0.00001 to about 45 mg/kg body weight, preferably from 0.001 to 15 mg/kg body weight most preferably 0.1 to 8 mg/kg body weight, of an anti-migraine and/or anti-nausea drug, from about 0.1 to about 25% of mucoadhesive agent promoting adhesion of the composition to the vaginal mucosa, from about 5 to about 30% of a permeation enhancer assuring transfer of the drug across the vaginal epithelium, and from about 40 to about 95% of a lipophilic or hydrophilic carrier serving as a vehicle for the drug and, optionally, from about 0 to about 30%, preferably about 1 to 5%, of a solubilizing agent for increased transport of released pharmacological agent into the systemic blood circulation.

Other pharmaceutically acceptable excipients suitable for vaginal delivery, such as buffers, fillers, stabilizers, emulsifiers, and any such other excipients as are known in the art to be useful for these purposes may also be added.

Any component and/or excipient used in formulations of this invention needs to be approved for human use and acceptable for use in the vagina with understanding that not all excipients approved for oral use may be approved and/or suitable for vaginal use.

The mucoadhesive composition is formulated as a solution, gel, cream, lotion, ointment, foam, film, suppository, liposomal suspension, microemulsion, capsule, tablet, microparticles, microcapsules, nanoparticles, or nanocapsules, and each formulation form is either incorporated within a fluid impermeable layer, cap or strip of a vaginal device or attached thereto.

The mucoadhesive composition formulated as above can be incorporated into the fluid impermeable layer, cap or strip of the vaginal device or be used as a coating for such layer, cap or strip. Alternatively, the composition may be incorporated into a sponge, foam, film, tablet, capsule, ring, mucoadhesive patch or iontophoretic system and any one of these may be placed within the fluid impermeable cap or attached to the fluid impermeable strip or layer. The vaginal device of the invention have already been described in section II.

Any form of drug delivery system that will effectively deliver the anti-migraine and/or anti-nausea agent to the vaginal mucosa or transmucosally across the vaginal epithelium into the general blood circulation is intended to be included within the scope of this invention.

A. Components of the Mucoadhesive Composition

Individual components of the mucoadhesive composition are the anti-migraine or anti-nausea drug, a mucoadhesive agent, a lipophilic or hydrophilic carrier and penetration enhancer or sorption promoter.

1. Anti-Migraine and Anti-Nausea Agents

The antimigraine therapeutic agents are pharmacologically active compounds effective in the treatment, management, and control of headache pain and have been already described.

In the mucoadhesive composition of the invention, the anti-migraine and anti-nausea drugs are present in doses ranging from ranging from 0.00001 to about 45 mg/kg body weight, preferably from 0.001 to 15 mg/kg, most preferably from 0.1 to 8 mg/kg body weight. Exemplary dosages for ergotamine, for example are in the range from about 0.05 to about 1.5 mg/kg t.i.d., diclofenac sodium from about 0.5 to about 4 mg/kg b.i.d., sumatriptan from about 0.2 to about 10 mg/kg per day, zolmitriptan from about 0.1 to 7 mg/kg per day, metoclopramide from about 0.1 to 1.0 mg/kg per dose, perchlorperazine from 0.3 to 2.5 mg/kg per dose, ondansetron from about 0.3 to 4 mg/kg per dose, dronabinol from about 0.05 to 0.5 mg/kg b.i.d., and promethazine from 0.15 to 1.3 mg/kg per dose. Suitable dosages for other anti-migraine or anti-nausea drugs are readily available from pharmaceutical sources.

The anti-migraine or anti-nausea drugs are formulated in said composition alone, in admixture of two or more or in admixture of the anti-migraine agent and an anti-nausea drug, and/or in combination with another pharmacologically effective agent or with an acceptable pharmaceutical excipient.

2. Mucoadhesive Agents

For vaginal delivery according to the invention, the mucoadhesive composition comprises, as an essential component, a mucoadhesive agent. The mucoadhesive agent permits a close and extended contact of the composition, or the drug released from said composition, with mucosal surface by promoting adherence of said composition or drug to the mucosa. The mucoadhesive agent is preferably a polymeric compound, such as preferably a cellulose derivative, but it may be also a natural gum, alginate, pectin, or such similar polymer. The most preferred cellulose derivative is hydroxypropyl methylcellulose available under the trade name METHOCEL®, commercially available from Dow Chemical Co.

The mucoadhesive agent is present in from about 0.1 to about 25%, by weight, preferably in from about 1.5 to about 15% and most preferably about 1.5-5%.

3. Sorption Promoters

The mucoadhesive composition additionally includes a sorption promoter present in from about 2 to about 30%, by weight. Sorption promoter assures a permeation and penetration of the drug through the vaginal mucosa, that is moving it through the vaginal mucosa and into systemic blood circulation.

Sorption promoters include non-ignitable glycol ester derivatives, such as polyethylene glycol caprylic/capric glycerides known as LABRASOL®, commercially available from Gattefossé, glycol derivatives with glycerol esters, such as oleic acid esters of propylene glycol and glycerol known as ARLACEL® 186, commercially available from Imperial Chemical Industries. Particularly preferred are non-ignitable glycol ether derivatives, such as, most preferably, ethoxydiglycol, known under its trade name TRANSCUTOL® and commercially available from Gattefossé, or interesterified stone oil, for example LABRAFIL M 1944CS, commercially available from Gattefossé. The interesterified stone oil is a vegetable oil ethoxylated by replacing a certain portion of glycerol of the glycerides contained in vegetable oil with polyoxyethylene-glycols.

4. Lipophilic and Hydrophilic Carriers

Depending on the drug affinity, the composition of the invention additionally comprises either the lipophilic or the hydrophilic carrier that is appropriate for the used anti-migraine or anti-nausea agent. Such carrier is typically present from about 30 to about 95%, by weight.

The carrier is selected from such compounds for which the drug has low affinity. Thus the lipophilic carrier is appropriate and selected for formulation of the hydrophilic anti-migraine or anti-nausea drug and the hydrophilic carrier is appropriate for formulation of the lipophilic anti-migraine or anti-nausea drug.

i. Lipophilic Carriers

Preferred lipophilic carriers for use with hydrophilic drugs include any medium chain triglycerides and/or a saturated mono-, di- or triglyceride of fatty acids, particularly those having carbon chain of from 8 to 18 carbons, or a mixture thereof. Examples of the lipophilic carrier are saturated glycerides known and available under the trade name SUPPO-CIRE® AS2 or CS2, and related compounds commercially available, for example, from Gattefossé, Westwood, N.J.

ii. Hydrophilic Carriers

Preferred hydrophilic carriers include polyethylene glycols of molecular weight between about 200 and 8000, OR derivatives or mixtures thereof, such as PEG 6000/PEG 1500, or PEG 6000/PEG 1500/PEG 400, or PEG 6000/PEG 400, or PEG 8000/PEG 1500, commercially available from, for example, Sigma/Aldrich, St. Louis, Mo.

5. Penetration Enhancers

Composition of the invention may additionally contain penetration enhancers, compounds which assist in improving penetration properties of the drug or their mixtures by changing the surface properties of the drugs or their mixtures, or drug containing solutions or suspensions. These compounds thus, in a way, act as solubilizers. Examples of the penetration enhancers are non-ionic surfactants.

The penetration enhancer may be added from about 1% to about 30%, as required.

6. Solubilizing Agents

The composition optionally includes also a solubilizing agent, such as complex-forming solubilizer citric acid, ethylenediamine-tetraacetate, sodium meta-phosphate, succinic acid, urea, cyclodextrin, polyvinylpyrrolidone, diethylammonium-ortho-benzoate, or micell-forming solubilizers such as Tween and spans, for example Tween 80. Other solubilizer useful for the compositions of this invention are polyoxyethylene sorbitan fatty acid ester, polyoxyethylene -alkyl ethers, n-alkyl amine n-oxides, poloxamers, organic solvents, phospholipids and cyclodextrines.

The solubilizing agents may be added from about 0.1% to about 30%.

7. Additional Excipients

The composition of the invention may additionally contain other excipients, such as, fillers, emulsifiers, stabilizers, buffers, and others, as appropriate. Examples of these excipients are isostearylstearate, isopropyl myristate, glycerin, mineral oil, polycarbophil, carbomer 934P or 940, hydrogenated palm oil, glyceride, sodium hydroxide, sorbic acid, and purified water.

B. Preferred Formulations

All formulations which contains components of the invention in ranges given above are intended to be within the scope of this invention. Few compositions presented here as preferred formulation are only exemplary and are not intended to limit the scope of the invention in any way.

Preferred formulations for a hydrophilic anti-migraine or anti-nausea drug comprise between about 0.01-10%, by weight, of the drug, about 60-90%, by weight, lipophilic carrier, between about 0.1-25%, by weight, mucoadhesive agent, between about 1-25%, by weight, sorption promoter and optionally a penetration enhancer or solubilizing agent, usually present in 1-30%, by weight.

Preferred formulations for the lipophilic drugs comprise between about 0.01-10%, by weight, of the drug, about 30-90%, by weight of hydrophilic carrier, between about 0.1-25%, by weight, of mucoadhesive agent, between 1 and 25% of sorption promoter and optionally between about 1-30%, by weight, solubilizing agent and/or permeation enhancer.

In one preferred embodiment of the invention, 0.01-10% of the drug is formulated with other components such as between about 60 to 90% by weight lipophilic carrier, between about 1.5 to 20% mucoadhesive agent, between about 10-20% of sorption promoter, between 0 to 30% solubilizing agent, and between about 1 to 30% permeation enhancer.

In another preferred embodiment of the invention, 0.01-10% drug is formulated in admixture with about 60 to 90%, by weight, of hydrophilic carrier, between about 1.5 and about 20% of mucoadhesive agent, between about 10 and 15% of sorption promoter and optionally between 0-30% of solubilizing agent and/or between about 1 and 30% of permeation enhancer.

In another preferred embodiment of the invention, the formulation contains 0.01-10% of a hydrophilic drug, 75% of a lipophilic carrier SUPPOCIRE® AS2, 2% hydroxypropyl methylcellulose, and 15% of ethoxydiglycol (TRANSCUTOL®).

In another preferred embodiment of the invention, the formulation includes 0.01-10% of a lipophilic drug, 75% of a hydrophilic carrier PEG 6000/PEG 1500, 2% hydroxypropyl methylcellulose, and 15% of ethoxydiglycol (TRANSCUTOL®).

C. Process for Formulating Hydrophilic or Lipophilic Anti-Migraine and Anti-Nausea Drugs The lipophilic or hydrophilic anti-migraine or anti-nausea agents or inhibitors of membrane efflux system are formulated using the following process.

In a general method for preparing a formulation for a hydrophilic drug, the lipophilic carrier is melted at 45-50° C. in a heated vessel. The mucoadhesive agent is added to the carrier with stirring. The preferred hydrophilic drug is dissolved in the sorption promoter combined with the penetration enhancer and solubilizing agent. This mixture is added to the carrier/mucoadhesive agent suspension. The final formulation is poured into molds of the desired size and shape or incorporated into a device of the invention. The molds which are stored in a refrigerator at 4-6° C.

In a general method for preparing a formulation including a lipophilic drug, the hydrophilic carrier is melted in a heated vessel at an appropriate temperature recommended by manufacturer. The mucoadhesive agent is added to the carrier with stirring. The preferred lipophilic drug is dissolved in the sorption promoter, and penetration enhancer combined with the solubilizing agent are optionally added. This mixture is admixed with the carrier/mucoadhesive agent suspension. The final formulation is poured into molds of the desired size and shape or incorporated into a device of the invention. The final formulation is then placed in a refrigerator at 4-6° C.

D. Sustained Release

In one embodiment, the mucoadhesive composition can be formulated as a sustained and controlled release drug system.

The anti-migraine or anti-nausea drug which is formulated for controlled and sustained release is formulated either for rapid, slow, continuous release or for pulsed delivery.

Continuous release or delivery means continuous and uninterrupted release of the drug from the formulation or device wherein the drug is formulated either in the matrix, microparticle, bioadhesive particle, liposomal suspension or any another system typically used for such release.

Pulsed release or delivery is a delivery of the drug in intermittent intervals. Such pulsed delivery may be provided, for example, by formulating the drug in the matrix, microparticle, bioadhesive particle, liposomal suspension or any another system, as described for continuous delivery, incorporated into individual fluid impermeable layers interspaced with inactive layer without drugs, such as for example, a layer of dissolvable coatings or by formulating the drug in different formulating agents. Methods and formulating agents for sustained delivery are known in the art.

A drug delivery system for a controlled release must be capable of controlled release of a drug into the vaginal mucosa over several hours or more. This is achieved by the addition of time release additives such as hydrogel-forming polymers or non-erodible matrices, etc., known in the art.

Additionally, during the menstrual cycle when the pH of the vagina changes, the drug delivery systems additionally may contain buffers to stabilize pH to enhance absorption.

E. Bioadhesive Systems and Microemulsions

Bioadhesive microparticles or bioadhesive nanoparticles constitute still another intravaginal drug delivery system suitable to be incorporated into the fluid impermeable layer for use in the present invention.

Bioadhesive systems and microemulsions are formulations particularly suitable for vaginal transmucosal delivery.

The microemulsion may contain pharmaceutically acceptable surfactants, for example, LABRASOL®, PLUROL® isostearate (Gattefossé), co-solvents such as isopropanol or ethanol, and water. Microemulsions containing one or more of the above components have been shown to improve bioavailability of anti-migraine or anti-nausea drugs.

The bioadhesive systems use derivatives of cellulose such as hydroxypropyl cellulose and polyacrylic acid. They release the anti-migraine or anti-nausea drugs for up to five days once they are placed in the appropriate formulation. This system represents a multi-phase liquid or semi-solid preparation which is easily incorporated into the fluid impermeable layers, caps or strips. The microparticles or nanoparticles cling to the wall of the vagina and release the drug over a several hour period of time. Many of these systems were designed for nasal use, as described in U.S. Pat. Nos. 4,756,907, and 6,200,590 incorporated herein by reference, but can be easily modified for use in the vagina. The bioadhesive system may comprise microparticles or nanoparticles filled with the anti-migraine or anti-nausea agent and may contain a surfactant for enhancing solubility and/or uptake of the drug. The microparticles have a diameter of 1-100 μm, whereas nanoparticles have a diameter of 10-1000 nm. Microparticles and nanoparticles can be prepared from starch, gelatin, albumin, collagen, or dextran according to methods known in the art.

All formulating options discussed above may be advantageously incorporated into the fluid impermeable layers, caps or strips of the vaginal device as described herein.

Bioadhesive tablets are another drug delivery system suitable for transmucosal delivery. These bioadhesive systems use hydroxypropyl cellulose and polyacrylic acid. They release drugs for up to five days once they are placed in the appropriate formulation. The tablet of the invention has the shape of a suppository or a tampon so that the maximum contact is achieved between the vaginal wall and the tablet surface or such a shape as is suitable for incorporation into the vaginal device of the invention.

The drug formulated in a bioadhesive system may also be incorporated into creams, lotions, foams, paste, ointments, microemulsions, liposomal suspensions, and gels which can be incorporated into the vaginal device. Processes for preparing pharmaceuticals in these vehicles can be found throughout the literature.

Suitable nontoxic pharmaceutically acceptable excipients for use in the compositions of the present invention will be apparent to those skilled in the art of pharmaceutical formulations and examples are described in REMINGTON: The Science and Practice of Pharmacy, 20$^{th}$ Edition, A. R. Gennaro, ed., (2000). The choice of suitable carriers will depend on the exact nature of the particular vaginal dosage form desired, e.g., whether the anti-migraine and/or anti-nausea agent is to be formulated into a cream, lotion, foam, ointment, paste, solution, microemulsions, liposomal suspension, microparticles, nanoparticles or gel, as well as on the physicochemical properties of the anti-migraine or anti-nausea drug.

Although the mucoadhesive compositions described above typically contain only one drug selected from the group of anti-migraine agents or anti-nausea for treatment of migraine or headache, nausea or vomiting, such compositions may additionally contain other pharmaceutical agents or a combination thereof, such as, for example, pain killers, antivirals, antipruritics, corticosteroids and other agents which may enhance the therapeutic effect of the primary drug.

All bioadhesive systems described above may be administered directly or via an intravaginal device.

IV. Method for Delivery of the Anti-Migraine/Anti-Nausea Drugs

A method of the invention is developed for and is particularly suitable for efficacious delivery of anti-migraine and anti-nausea drug for elimination and reduction of symptoms of nausea and vomiting. Efficacy of the anti-migraine and anti-nausea drugs is enhanced due to bypassing extensive hepatic first-pass deactivation of anti-migraine and/or anti-nausea drugs.

The method, useful for treatment, management, and control of headache pain, nausea, and vomiting, that are primary symptoms associated with migraine but are not only limited to this condition but can also occur as a result of other conditions such as administration of chemotherapeutic drugs or surgery as described in detail above, comprises steps of contacting the vaginal mucosa lining the vaginal cavity with an vaginal device incorporated with a mucoadhesive composition comprising anti-migraine and/or anti-nausea drugs. Said composition comprises at least one anti-migraine drug or one anti-nausea drug selected from the group consisting of ergot alkaloids and derivatives, antihistamines, barbiturates, nonsteroidal anti-inflammatory agents, analgesics, serotonin antagonists, neurokinin-1 antagonists, cannabinoids, calcitonin gene-related peptide (CGRP) antagonists, steroids, sympathomimetics, tranquilizers, and antiepileptics, alone or in combination with another anti-migraine drug or said anti-nausea agent, or in combination with another pharmaceutical agent or a pharmaceutically acceptable excipient, and maintaining said composition or device in contact with said vaginal mucosa for a period of time permitting a rapid or slow, continuous or pulsed delivery of the drug to or through the vaginal mucosa and necessary to deliver a therapeutic dose of the anti-migraine and/or anti-nausea drug. Such time is typically from several minutes to several hours.

The delivery route utilizes the mucoadhesive composition incorporated into a fluid impermeable layer or layers of a vaginal device for transmucosal delivery and comprises delivery of a combination of the anti-migraine and/or anti-nausea agent with optionally added mucoadhesive agents, carriers, permeation enhancing agents and solubilizing excipients for transvaginal delivery.

Additionally, more than one therapeutic or palliative agents may be added to the mucoadhesive anti-migraine or anti-nausea composition and/or any other pharmacologically active agent suitable for the treatment, management, and control of headache pain, nausea and vomiting may also be added. All combinations and variations are intended to be within the scope of the invention.

The current method, therefore, also includes the delivery of anti-migraine or anti-nausea drugs in combination with drugs that reduce inflammation, have analgesic effects, modulate cerebral blood flow, and such other therapeutically active agents.

The method is practiced by incorporating the mucoadhesive composition comprising an anti-migraine and/or anti-nausea drug into or attaching it to the fluid impermeable layer, cap or strip of the vaginal device and by inserting said vaginal device inti vagina. The mucoadhesive composition is formulated as a solution, gel, cream, lotion, ointment, foam, film, suppository, liposomal suspension, microemulsion, capsule, tablet, microparticles, microcapsules, nanoparticles, nanocapsules. The device suitable for these purposes is selected from the group consisting of a vaginal tampon, vaginal ring, vaginal pessary, vaginal sponge, vaginal tablet, vaginal capsule, vaginal patch, vaginal iontophoretic system or vaginal cup.

The direct contact of the mucoadhesive composition with the vaginal mucosa permits an immediate rapid or slow, extended continuous, or intermittent, pulsed delivery of the drug that leads to efficacious treatment. The mucoadhesive composition attached to or incorporated into a fluid impermeable layer of the vaginal device permits use of only such a dosage of the anti-migraine and/or anti-nausea drug as is therapeutically required for systemic treatment of the migraine or nausea.

The above-described approach for transmucosal drug delivery is based on the concept that the upper vagina and the uterus have specific blood flow characteristics, either by a portal type circulation or by venous and lymphatic channels, permitting preferential transport and delivery of pharmacological agents from the vaginal mucosa directly to the systemic blood circulation, thereby bypassing the gastrointestinal tract and liver, where most of anti-migraine and/or anti-nausea drugs experience a substantial deactivation and elimination through metabolism.

The most specific demonstration of the transvaginal concept has been achieved by inventors with several types of drugs, as described in patents U.S. Pat. Nos. 6,086,909, and 6,197,327, 6,461,779 B1, and 6,572,874 incorporated by reference. Anti-migraine agents and/or anti-nausea drugs, when properly formulated, are transported through the vaginal wall in the same manner as described in the above patents.

UTILITY

The invention is useful for delivery of an anti-migraine or anti-nausea drug to the uterus or to the systemic circulation of a female subject. The invention provides several previously unrecognized improvements. The newly described approach prevents the absorption of the pharmaceutical composition into the porous portion of the tampon and thus becoming unavailable for drug delivery. The new approach provides a more efficacious delivery of the an anti-migraine or anti-nausea drug to the uterus or to the systemic circulation. The whole amount of drug released from the composition is available for absorption into the vaginal mucosa instead of being only partially delivered to the vaginal mucosa and partially absorbed by the tampon.

In practice, the drug delivery system, that is a composition or a device of the invention, are applied or administered upon diagnosis of migraine or nausea. Typically, the treatment is continued for as long as needed to treat the headache, nausea or vomiting, to maintain state or prevent further growth.

EXAMPLE 1

Preparation of Sumatriptan Vaginal Suppository

This example describes a process for preparation of intravaginal suppositories or incorporation into the fluid impermeable coating.

The dose of sumatriptan (Global Trade Alliance, Scottsdale, Ariz.) was 20 mg. Vaginal suppositories were formulated and prepared 24 hours prior to administration. The four basic ingredients for the suppositories were distilled water (15% wt), SUPPOCIRE AS2X (Gattefossé, Westwood, N.J.) (67.5% wt), hydroxypropyl methylcellulose (HPMC) (obtained as METHOCEL® K, HPMC K15M, from Dow Chemical, Midland, Mich.) (1.5% wt), a mucoadhesive agent, and TRANSCUTOL® (Gattefossé) (15% wt), a permeation enhancer.

To make eight suppositories, 10.8 grams of SUPPOCIRE, 240 mg of HPMC, 2.4 grams of TRANSCUTOL, and the calculated dose of the drug were weighed out. SUPPOCIRE was melted in a disposable 100 mL polypropylene beaker suspended in a water bath at 50° C. The solution was stirred until completely melted. HPMC and TRANSCUTOL were then added and mixed. Finally, the drug was added combined with 2.4 grams of distilled water. After sufficient mixing, the warm suppository mass was quickly poured into commercial nickel-plated brass suppository molds available from the Adelphi Group of Company (West Sussex, UK). Suppositories were kept refrigerated until use.

EXAMPLE 2

Preparation of Metoclopramide Vaginal Suppository

This example describes the preparation of metoclopramide-containing vaginal suppositories for incorporation into the fluid impermeable coating.

Metoclopramide hydrochloride is commercially obtained from ICN Biomedicals, Inc. (Costa Mesa, Calif.). Vaginal suppositories comprising a dose of 50 mg per suppository were prepared using the method identical to the procedure described for sumatriptan suppositories. The composition of the pharmaceutical excipients in these formulations was SUPPOCIRE AS2X (66% wt), HPMC (1.5% wt), TRANSCUTOL (15% wt), and distilled water (15% wt).

Suppositories comprising other anti-migraine or anti-nausea drugs are prepared the same way except that their amount, including of excipients, may vary.

EXAMPLE 3

Preparation of Diclofenac Sodium Vaginal Suppository

This example describes the procedure for preparation of hydrophilic diclofenac vaginal suppositories for incorporation into a fluid impermeable coating.

A binary mixture of 7.18 grams of polyethylene glycol (PEG) 3350 and 3.86 grams of PEG 6000 (Fisher Scientific, Pittsburgh, Pa.) is melted on a water bath. To the homogenous PEG solution 400 mg of triethanolamine (Sigma/Aldrich, St. Louis, Mo.) is added. In a separate container, 400 mg diclofenac sodium (Spectrum Chemicals & Laboratory Products, Gardena, Calif.) is dissolved in 2.4 grams of TRANSCUTOL that is further diluted with 2.4 grams of distilled water. Both solutions are combined and cooled under stirring. After reaching suitable viscosity, aliquots of the suppository mass are filled into nickel-plated brass molds.

EXAMPLE 4

Preparation of Promethazine Vaginal Film

This example describes the process for preparation of vaginal film composition for incorporation into the fluid impermeable coating.

In a 100 mg glass beaker, 240 mg promethazine hydrochloride (Spectrum Chemicals & Laboratory Products, Gardena, Calif.) is dissolved in 2 grams of distilled water and 1.5 grams of TRANSCUTOL. This drug solution is combined with a polymeric alginic acid solution consisting of 500 mg alginic acid, sodium salt (CarboMer, Inc., Westborough, Mass.) and 8 grams of water. Thin films of approximately 1 mm in thickness will be prepared using a hand-operated CAMAG TLC plate coater (CAMAG Scientific, Inc., Wilmington, N.C.).

EXAMPLE 5

Preparation of Metoclopramide Vaginal Foam

This example describes the preparation of a medicated vaginal foam.

Metoclopramide hydrochloride (ICN Biomedicals, Inc., Costa Mesa, Calif.) is dissolved in a mixture of PEG 400 (10% wt, Fisher Scientific, Pittsburgh, Pa.) and TRANSCUTOL (15% wt). In a separate container 4.5% (wt) alginic acid, sodium salt is dissolved in distilled water (70% wt). Both solutions are combined and aliquots of 5 mL filled into plastic syringe. Following a thorough freezing process at −80° C., the samples were removed from the syringe mold and lyophilized to form the medicated vaginal foam.

What is claimed is:

1. A vaginal device for delivering an anti-migraine or anti-nausea drug to a female subject, said device comprising
    the vaginal device;
    the anti-migraine or anti-nausea drug formulated as a mucoadhesive composition; and
    a fluid impermeable coating comprising said composition;
    wherein said vaginal device is a tampon, foam, ring, pessary, sponge, cylinder, tablet, capsule, pad, suppository, pellet or tube;
    wherein said anti-migraine drug is selected from the group of compounds consisting of ergotamine, dihydroergotamine, ergostine, butalbital, phenobarbital, acetaminophen, diclofenac sodium, ketoprofen, ketorolac, ibuprofen, piroxicam, naproxen, acetylsalicylic acid, flurbiprofen, tolfenamic acid, butorphanol, meperidine, methadone, sumatriptan, naratriptan, razatriptan, zolmitriptan, almotriptan, eletriptan, dexamethasone, hydrocortisone, isometheptene, chlorpromazine, diazepam, droperidol, valproic acid, gabapentin, topiramate and divalproex sodium, each alone or in combination, or in combination with the anti-nausea drug, and
    wherein said anti-nausea drug is selected from the group consisting of metoclopramide, prochlorperazine, domperidone, ondansetron, tropisetron, dolasetron, nabilone, dronabinol, levonantradol, aprepitant, cyclizine, promethazine, each alone or in combination or in combination with the anti-migraine drug;
    wherein said fluid impermeable coating is a degradable or non-degradable water soluble or non-soluble polymer selected from the group consisting of wax, plastic polymeric film, coated gauze, synthetic polymer, dextran, cellulose, hydroxypropyl methylcellulose, hydroxypropyl cellulose, hydroxyethyl cellulose, sodium carboxymethyl cellulose, polyethylene glycol, polyethylene, polyethylene oxide, alginate, chitosan, copolymer of ethylene oxide and propylene oxide, polyethylene oxide-co-propylene oxide, polyacrylic acid, collagen, albumin, gelatin, polylactide, polyglycolide, polyethylene terephthalate, polybutyric acid, polyvaleric acid, polylactide-co-caprolactone, polyanhydride, polyorthoester, polyamide, polypropylene, polystyrene, polyvinyl chloride, polymethacrylic acid and a derivative thereof, alone, or in combination,
    wherein said coating is attached to said device as a film, foil, sheet, beads or xerogel and is either incorporated into said device, attached to said device or inserted into said device.

2. The device of claim 1 wherein said mucoadhesive composition comprises from about 0.00001 to about 45 mg/kg of body weight of the anti-migraine or anti-nausea drug, from about 0.1 to about 25%, by weight, of a mucoadhesive agent, from about 30 to about 95%, by weight, of a lipophilic or hydrophilic carrier, and from about 5 to about 30% of a sorption promoter.

3. The device of claim 2 wherein said coating is incorporated with said mucoadhesive composition or said composition is attached to said coating.

4. The device of claim 3 wherein said vaginal device is completely or partially coated with said fluid impermeable material.

5. The device of claim 4 wherein said vaginal device is coated with said fluid impermeable material partially at the proximal end.

6. The device of claim 4 wherein said coating comprising said composition is attached to said device and configured to make physical contact with the vaginal mucosa and cervix of the uterus.

7. The device of claim 6 wherein said coating is attached to said device permanently or removably as a cap, cup or strip.

8. The device of claim 7 wherein said cap, cup or strip is attached to said device permanently and wherein said mucoadhesive composition is formulated as a foam, film, suppository, tablet, capsule or capsule containing microparticle or nanoparticle and is attached or inserted into said cap, cup or strip.

9. The device of claim 7 wherein said cap, cup or strip is attached to said device permanently and wherein said mucoadhesive composition is formulated as a solution, powder, cream, lotion, microparticle, nanoparticle, emulsion, liposomal suspension fluid, a bioadhesive system or microemulsion and incorporated into said cap, cup or strip.

10. The device according to claim 3 wherein said mucoadhesive composition comprises from about 0.001 to about 15 mg/kg of body weight the anti-migraine or anti-nausea drug, from about 40 to about 95% of a lipophilic or hydrophilic carrier, from about 1.5 to about 15%, by weight, of the mucoadhesive agent, from about 2 to about 30%, by weight, of sorption promoter and additionally from about 5 to about 30% of a permeation enhancer.

11. The device of claim 10 wherein said mucoadhesive agent is hydroxypropyl methylcellulose, a cellulose derivative, a natural gum, alginate or pectin, wherein said sorption promoter is ethoxydiglycol, polyethylene glycol caprylic/capric glycerides, a glycol derivative with oleic acid esters of propylene glycol and glycerol or interesterified stone oil, wherein the lipophilic carrier is a saturated mono-, di- or triglyceride of fatty acids having carbon chain of from 8 to 18 carbons, or a mixture thereof and wherein the hydrophilic carrier is a polyethylene glycols (PEG) of a molecular weight between about 200 and 8000, or a derivative or mixture thereof, PEG 6000/PEG 1500, PEG 6000/PEG 1500/PEG 400, or PEG 6000/PEG 400, or PEG 8000/PEG 1500.

12. The device of claim 1 wherein said device is a tampon or foam and wherein said fluid impermeable coating material is polyethylene oxide.

13. The device of claim 10 wherein said anti-migraine or anti-nausea drug is ergotamine in the range from about 0.05 to about 1.5 mg/kg, t.i.d., diclofenac sodium from about 0.5 to about 4 mg/kg, b.i.d., sumatriptan from about 0.2 to about 10 mg/kg per day, zolmitriptan from about 0.1 to 7 mg/kg per day, metoclopramide from about 0.1 to 1.0 mg/kg per dose, perchlorperazine from 0.3 to 2.5 mg/kg per dose, ondansetron from about 0.3 to 4 mg/kg per dose, dronabinol from about 0.05 to 0.5 mg/kg, or promethazine from 0.15 to 1.3 mg/kg.

* * * * *